(12) United States Patent
Roy et al.

(10) Patent No.: US 8,796,484 B2
(45) Date of Patent: Aug. 5, 2014

(54) POLYMERIZABLE SILICONE COPOLYOL MACROMERS AND POLYMERS MADE THEREFROM

(71) Applicant: Lubrizol Advanced Materials, Inc., Cleveland, OH (US)

(72) Inventors: Aroop K. Roy, Mechanicville, NY (US); Krishnan Tamareselvy, Brecksville, OH (US)

(73) Assignee: Lubrizol Advanced Materials, Inc., Cleveland, OH (US)

(*) Notice: Subject to any disclaimer, the term of this patent is extended or adjusted under 35 U.S.C. 154(b) by 0 days.

(21) Appl. No.: 13/742,391

(22) Filed: Jan. 16, 2013

(65) Prior Publication Data

US 2013/0137844 A1 May 30, 2013

Related U.S. Application Data

(62) Division of application No. 11/677,610, filed on Feb. 22, 2007, now abandoned.

(60) Provisional application No. 60/776,611, filed on Feb. 24, 2006.

(51) Int. Cl.
| | |
|---|---|
| *C08G 77/50* | (2006.01) |
| *A61K 8/891* | (2006.01) |
| *A61K 8/894* | (2006.01) |
| *A61K 8/895* | (2006.01) |
| *C08G 77/20* | (2006.01) |
| *C08F 283/00* | (2006.01) |
| *C08L 83/12* | (2006.01) |
| *C08G 77/38* | (2006.01) |

(52) U.S. Cl.
USPC ........... 556/450; 556/453; 556/463; 556/436; 556/465; 556/466; 528/26; 528/29

(58) Field of Classification Search
CPC ........ C08G 77/50; C08G 77/20; C08G 77/38; A61K 8/881; A61K 8/894; A61K 8/895; C08F 283/00; C08L 83/12
USPC ......... 556/450, 453, 562, 463, 436, 437, 465, 556/466; 528/26, 29
See application file for complete search history.

(56) References Cited

U.S. PATENT DOCUMENTS

| | | | |
|---|---|---|---|
| 3,560,544 A * | 2/1971 | Haluska | ........................ 556/437 |
| 4,384,096 A | 5/1983 | Sonnabend | |
| 4,421,902 A | 12/1983 | Chang et al. | |
| 4,514,552 A | 4/1985 | Shay et al. | |
| 4,600,761 A | 7/1986 | Ruffner et al. | |
| 4,616,074 A | 10/1986 | Ruffner | |
| 4,693,935 A | 9/1987 | Mazurek | |
| RE33,156 E | 1/1990 | Shay et al. | |
| 5,011,978 A | 4/1991 | Barron et al. | |
| 5,136,063 A | 8/1992 | O'Lenick, Jr. | |
| 5,162,472 A | 11/1992 | O'Lenick, Jr. | |
| 5,180,843 A | 1/1993 | O'Lenick, Jr. | |
| 5,248,783 A * | 9/1993 | O'Lenick | ...................... 548/110 |
| 5,292,843 A | 3/1994 | Jenkins et al. | |
| 5,294,692 A | 3/1994 | Barron et al. | |
| 5,296,625 A | 3/1994 | O'Lenick, Jr. et al. | |
| 5,385,999 A | 1/1995 | D'Anvers et al. | |
| 5,412,142 A | 5/1995 | Wilkerson, III et al. | |
| 5,433,753 A | 7/1995 | Dahmen et al. | |
| 5,770,760 A | 6/1998 | Robinson | |
| 6,140,435 A | 10/2000 | Zanotti-Russo | |
| 6,197,317 B1 | 3/2001 | Klein | |
| 6,403,074 B1 | 6/2002 | Blankenburg et al. | |
| 8,021,650 B2 | 9/2011 | Tamareselvy et al. | |
| 2003/0211051 A1 | 11/2003 | Majeti et al. | |
| 2004/0038151 A1 | 2/2004 | Berger et al. | |
| 2004/0087469 A1 | 5/2004 | Carswell | |
| 2005/0158268 A1* | 7/2005 | Schmucker-Castner et al. | ........................ 424/70.16 |

FOREIGN PATENT DOCUMENTS

| | | |
|---|---|---|
| JP | 60-094486 | 5/1985 |
| JP | 07-500866 A | 1/1995 |
| JP | 08-134153 A | 5/1996 |
| WO | 2004/112733 A1 | 12/2004 |
| WO | 2004/113390 A1 | 12/2004 |
| WO | 2005/056625 A1 | 6/2005 |
| WO | 2007/035315 A2 | 3/2007 |

* cited by examiner

*Primary Examiner* — Michael M Bernshteyn
(74) *Attorney, Agent, or Firm* — Thoburn T. Dunlap

(57) ABSTRACT

A polymerizable dimethicone copolyol macromer composition is synthesized by reacting itaconic anhydride with a dimethicone copolyol. During the reaction itaconic anhydride spontaneously isomerizes to citraconic anhydride which in turn is esterified by the dimethicone copolyol. The obtained macromers are copolymerizable with olefinically unsaturated monomers. Polymers containing the macromer repeating units are useful in a variety of applications including personal care, textile and industrial formulations to deliver softness, lubricity, fixative, water repellency, gloss, surface modification, and surfactant properties.

13 Claims, No Drawings

POLYMERIZABLE SILICONE COPOLYOL MACROMERS AND POLYMERS MADE THEREFROM

RELATED U.S. APPLICATION

This application is a divisional application of co-pending U.S. patent application Ser. No. 11/677,610, filed on Feb. 22, 2007, which claims priority to Provisional Application Ser. No. 60/776,611, filed on Feb. 24, 2006.

FIELD OF THE INVENTION

The present invention relates to polymerizable dimethicone copolyol macromers containing ethylenic unsaturation and to polymers obtained therefrom. The ethylenically polymerizable macromer is formed from the reaction of a dimethicone copolyol containing terminal or pendant hydroxyl groups and itaconic anhydride. The obtained macromer is homopolymerizable or copolymerizable with ethylenically unsaturated monomers.

BACKGROUND

A class of silicon containing polymers known as polydimethylsiloxanes is widely employed in the coatings and personal care industries. In coatings formulations, polydimethylsiloxane and its derivatives are being increasingly used for general modification of surface properties as they provide water and oil repellency, stain resistance, barrier properties, surfactant properties and lubricity. In personal care formulations, the use of polydimethylsiloxane and derivatives thereof, particularly dimethicone copolyols, has gained wide acceptance for the latter's surfactant characteristics and positive effect on sensory properties of a given composition.

Attempts to improve the physical properties of such formulations by incorporating dimethicone copolyols into the composition have met with limited success. These polydimethylsiloxane derivatives were frequently incompatible with the polar polymers and/or other ingredients typically contained in coatings and personal care compositions. Often times auxiliary additives have to be employed to compatibilize the polydimethylsiloxane derivative and the anionic and cationic polymers typically used in the coatings and personal care industries to prevent phase separation of the key components during extended storage periods.

Accordingly, efforts have been made to covalently incorporate the polydimethylsiloxane derivatives into the target polymer backbone in an effort to compatibilize the silicone and polymer components of the formulation. U.S. Pat. No. 6,403,074 discloses a silicone containing polymer obtained by polymerizing ethylenically unsaturated monomers in the presence of dimethicone copolyol via a free radical mechanism. The patent disclosure surmises that grafting of the monomers onto the dimethicone copolyol occurs during the polymerization reaction. However, it is not evident from the disclosure to what extent (if any) that the dimethicone copolyol is covalently incorporated into the polymer backbone or whether an interpolymer of the dimethicone copolyol and the free radically polymerized monomers is formed. For polyhydroxy carbinol compounds, chain transfer can often be a significant problem during free radical polymerization, and this may prevent effective copolymerization of such compounds with other ethylenically unsaturated monomers.

In another approach, silicone containing macromers containing terminal unsaturation have been synthesized via the anionic polymerization of hexamethylcylotrisiloxane monomer (D3) to from a living polymer of controlled molecular weight. Termination of the anionic polymerization reaction is achieved via the direct reaction of the living polymeric anion with halogen-containing termination agents, such as, chlorosilane compounds containing a polymerizable vinyl group. The obtained vinyl terminated siloxane containing macromers in turn can be polymerized with other copolymerizable unsaturated monomers to obtain silicone containing copolymers as disclosed in U.S. Pat. Nos. 4,693,935 and 4,728,571. However, the synthesis of these macromers is very difficult and given the relatively high molecular weight of the macromer it is arduous to separate the unreacted impurities from the reaction product.

In U.S. Pat. No. 5,162,472, there is disclosed a vinyl terminated dimethicone copolyol macromer that is prophetically reported to be synthesized by esterifying acrylic acid with a hydroxyl terminated dimethicone copolyol. The reaction mass is heated to 140 to 180° C. and the disclosure states that the purportedly obtained vinyl containing silicone ester is subsequently copolymerized without additional purification. As is well known, the esterification of carboxylic acid with an alcohol is a slow reaction with moderate yields for oligomeric or polymeric substrates. Further, it is also well known in the art of acrylic acid chemistry that this highly reactive monomer spontaneously dimerizes at room temperatures via a thermally induced ionic mechanism wherein the proton dissociates from the carboxylic acid group forming a carboxylate anion which subsequently adds to acrylic acid via Michael-type addition to give the dimer. This phenomenon is substantially accelerated at increasing temperatures. At the reaction temperatures reported in the '472 disclosure the acrylic acid starting material would rapidly dimerize consuming most if not all of this reactant to yield a complex mixture of products. Given that the esterification of a carboxylic acid with an alcohol is slow and that acrylic acid rapidly oligomerizes at the reaction temperatures reported in the '472 disclosure, it is difficult to perceive how the purported product is obtained. Even if some product is formed it would be difficult, time consuming, and costly to separate the desired product from the reaction mass.

A more traditional esterification procedure for functionalizing a dimethicone copolyol with a vinyl end group is to react an acid chloride such as acryloyl chloride with the dimethicone copolyol and employing a base to remove the liberated HCl. The use of the acryloyl chloride eliminates the spontaneous oligomerization issues suffered from the use of acrylic acid as set forth in the '472 disclosure. However, a salt is generated as a by-product of the esterification reaction. Salts are not only difficult to remove from macromers but may also be deleterious to the subsequent polymerization of the macromer.

In addition to the problems faced in synthesizing the foregoing macromers, the polymerization activities of these acrylate-type macromers are similar to the polymerization activities of the comonomers intended for copolymerization into the polymer backbone, due to the unhindered nature of the carbon-carbon unsaturation in the terminal vinyl group. It is common practice to vary monomer reactivity as one approach to altering the copolymer structure and thereby the latter's physical and chemical properties.

Accordingly, there is a need for newer silicone containing macromers that are easily synthesized and purified and exhibit polymerization activities that allow flexibility in copolymerization to generate copolymers with desirable properties. We have now unexpectedly discovered such a silicone macromer via a reaction originally intended to prepare readily polymerizable compounds containing the itaconate moiety.

The present invention provides dimethicone copolyol macromers that are easily synthesized and that have unexpected polymerization activities which allow ready copolymerization to generate products with desirable properties. The copolyol macromers of the invention are synthesized from the reaction of a dimethicone copolyol and itaconic anhydride. Dimethicone copolyols contain terminal or pendant polyether groups that terminate in an active hydroxyl group. The reaction of a hydroxy silicone compound such as dimethicone copolyol with a cyclic anhydride is known. As disclosed in U.S. Pat. Nos. 3,560,544 and 5,296,625 the reaction of the active hydroxyl group(s) on the copolyol with the anhydride yields the copolyol half-ester of the anhydride. While these patents disclose the reaction of a dimethicone copolyol with a variety of cyclic anhydrides (including the olefinically unsaturated maleic anhydride), the use of anhydrides containing exocylic olefinic unsaturation is not described or suggested. Moreover, the '544 patent mentions that the derivatized silicone polymer is used as a surfactant, a wetting agent, detergent, emulsifier or fiber lubricant, and the '625 disclosure teaches that the obtained esters are useful in textile and personal care applications to render softness and lubrication to treated substrates. There is no teaching or suggestion in any of these disclosures that the reaction product of a hydroxy silicone with an anhydride containing any type of unsaturation can be employed as polymerizable macromer in the synthesis of polymers and copolymers.

Unexpectedly, it has been discovered that the half-ester formed from the reaction of itaconic anhydride (containing exocylic unsaturation) with a dimethicone copolyol yields a mixture of various isomers of citraconate mono-esters formed from the rapid isomerization itaconic anhydride to citraconic anhydride and subsequent reaction of the citraconic anhydride with the silicone copolyol. More surprisingly, given that the olefinic double bond in the citraconate moiety of the so-formed macromer is sterically encumbered by triple substitution, and the well known fact that trisubstituted olefins do not readily free radically polymerize at useful rates, we have found the citraconate dimethicone copolyol esters are easily copolymerized with a variety of monomers containing free radically polymerizable olefinic unsaturation. This is a novel and unexpected finding in the preparation of ethylenically unsaturated silicone copolyol esters. Itaconic anhydride is known to react with alcohols to generate the expected itaconate esters.

DESCRIPTION OF EXEMPLARY EMBODIMENTS

The dimethicone copolyol macromers of the present invention are obtained from the isomerization of itaconic anhydride and the subsequent esterification of isomerization products with a hydroxy containing dimethicone copolyol. Itaconic anhydride contains exocylic unsaturation as set forth in the structure below:

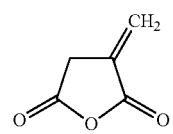

The exocylic unsaturation is depicted as the carbon-carbon double bond between the ring carbon atom and the alkylidene, e.g., methylene, group.

In the reaction medium comprising a dimethicone copolyol (DMC-OH) and itaconic anhydride, the itaconic anhydride nearly instantaneously isomerizes to citraconic anhydride which then reacts with the copolyol to give the citraconate dimethicone copolyol ester (and the regio- and stereo isomers thereof). Minor amounts of the regio-isomers of itaconate esters are also formed. An illustrative general reaction scheme is as follows:

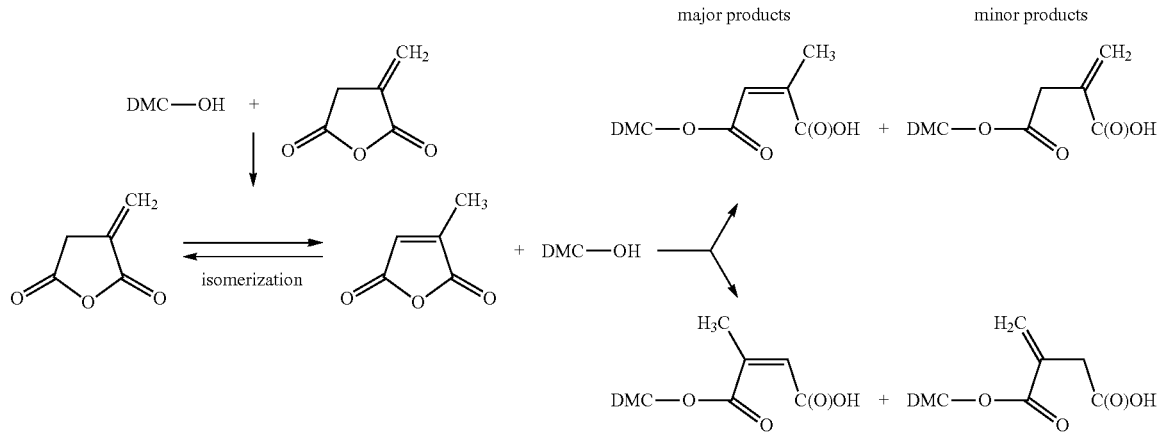

Minor amounts (less than 10 weight percent of the total ester formed) of the itaconate ester are formed due to an equilibrium between the citraconic anhydride and itaconic anhydride.

It is to be noted that the dimethicone copolyol represented by DMC-OH contains one or more anhydride reactive hydroxyl groups that can be located at a terminal end(s) of the dimethicone backbone or can be located as part of one or more pendant groups on the dimethicone backbone. Representative dimethicone copolyols are set forth under Formulae I and II below.

The esterification reaction can be carried out with or without a catalyst. When conducting the esterification reaction without catalyst the reaction mixture is heated to reaction temperatures of about 75° C. to about 90° C. The reaction can be run with either a stoichiometric amount of the dimethicone copolyol (based on the OH number) and the anhydride, or a slight excess of either reactant. In one embodiment of the invention, the amount of anhydride loading to dimethicone copolyol in the reaction mixture ranges between 0.1 equivalent to 1 equivalent based on the OH number of the dimethicone copolyol. In another embodiment the loading of anhydride to dimethicone copolyol is between 0.25 equivalent to 0.75 equivalent based on the OH number of the copolyol, and in still another embodiment the loading is between 0.5 equivalent to 0.75 equivalent. The reaction can be carried out from 1 to 3 hours. The reaction is conducted under an inert atmosphere such as a nitrogen blanket and can be carried out in a suitable solvent.

When carrying out the reaction in the presence of an esterification catalyst, the reaction rates are significantly accelerated. Standard esterification catalysts can be used at concentrations of between 0.05 percent to 0.50 percent based on the weight of the anhydride and the dimethicone copolyol in the reaction mixture. Suitable esterification catalysts include but are not limited to sulfuric acid, elemental tin, elemental zinc, elemental titanium, organo titanate compounds, organo tin compounds, organo zinc compounds, zinc oxide, magnesium oxide, calcium oxide, stannous oxide, and the alkali metal acetates such as sodium acetate and potassium acetate. Reaction temperatures can range from ambient room temperature to about 90° C. Typically ambient room temperature ranges from about 20° C. to about 26° C. All other reaction conditions are as above for the non-catalyzed reactions.

In another embodiment of the invention, citraconic anhydride which has methyl substitution on the double bond can be used in lieu of itaconic anhydride in the esterification reaction.

In one embodiment of the invention the dimethicone copolyol suitable for the esterification reaction contains a terminal hydroxy end group(s) and can be represented by Formula I below:

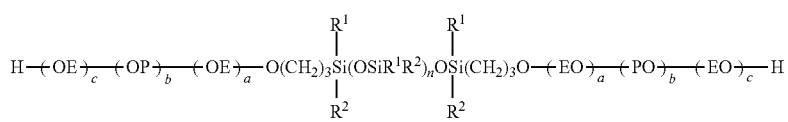

Formula I wherein $R^1$ and $R^2$ independently represent a radical selected from $C_1$ to $C_{30}$ alkyl, $C_1$ to $C_{20}$ halo substituted alkyl (e.g., $-CCl_3$, $-CBr_3$, $CF_3$), $C_3$ to $C_8$ cycloalkyl, $C_6$ to $C_{14}$ aryl, and $C_2$ to $C_{20}$ alkenyl; E represents a divalent ethylene radical ($-CH_2CH_2-$); P independently represents a divalent propylene radical ($-CH_2CH(CH_3)-$) or ($-CH_2CH_2CH_2-$); a, b, and c are independently 0 to 100; and n is 0 to 200. E taken together with the oxygen atom to which is attached represents an ethylene oxide residue (EO or OE) and P taken together with the oxygen atom to which it is attached represents a propylene oxide residue (PO or OP). The EO/PO residues can be arranged in random, non-random, or blocky sequences. As used here and throughout the specification the terms halogen and halo include but are not limited to bromo, chloro, and fluoro.

Exemplary $R^1$ and $R^2$ radicals include but are not limited to methyl, ethyl, propyl, butyl, pentyl, hexyl, cyclopentyl, cyclohexyl, phenyl, vinyl, and allyl. Each of the foregoing radicals as well as the generic $R^1$ and $R^2$ radicals set forth above are optionally substituted with $C_1$ to $C_5$ alkyl, halogen, and halo($C_1$ to $C_5$)alkyl (e.g., $-CCl_3$, $-CBr_3$, $CF_3$).

In one embodiment of the invention the dimethicone copolyol suitable for the esterification reaction contains a pendant hydroxy group(s) and can be represented by Formula II below:

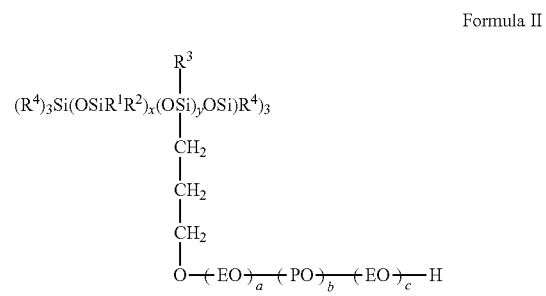

Formula II wherein $R^3$ represents a radical selected from $C_1$ to $C_{30}$ alkyl, halo($C_1$ to $C_{20}$) alkyl (e.g., $-CCl_3$, $-CBr_3$, $CF_3$), $C_3$ to $C_8$ cycloalkyl, $C_6$ to $C_{14}$ aryl, and $C_2$ to $C_{20}$ alkenyl; $R^4$ independently represents a radical selected from $C_1$ to $C_{30}$ alkyl, $C_6$ to $C_{14}$ aryl, and $C_2$ to $C_{20}$ alkenyl; EO (OE) and PO(OP) represent ethylene oxide and propylene oxide residues as previously defined; a, b, and c are independently 0 to 100; x is 0 to 200; and y is 1 to 200. The EO/PO residues can be arranged in random, non-random, or blocky sequences.

Exemplary $R^3$ radicals include but are not limited to methyl, ethyl, propyl, butyl, pentyl, hexyl, cyclopentyl, cyclohexyl, phenyl, vinyl, and allyl. Each of the foregoing radicals as well as the generic $R^3$ radicals described above are optionally substituted with $C_1$ to $C_5$ alkyl, halogen, and halo ($C_1$ to $C_{20}$) alkyl (e.g., $-CCl_3$, $-CBr_3$, $CF_3$).

Exemplary $R^4$ radicals include but are not limited to methyl, phenyl, and vinyl. Each of the foregoing radicals as well as the generic $R^4$ radicals described above are optionally substituted with $C_1$ to $C_5$ alkyl, halogen, and halo($C_1$ to $C_{20}$) alkyl (e.g., $-CCl_3$, $-CBr_3$, $CF_3$).

Exemplary dimethicone copolyol reactant materials suitable for the esterification are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi) and DC 5103 (Dow Corning Corporation).

An exemplary reaction scheme illustrating the esterification of a dimethicone copolyol of Formula I is as follows:

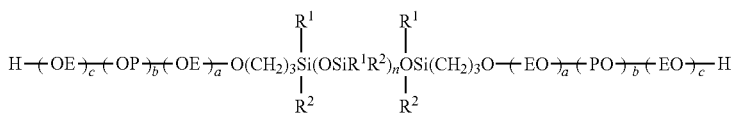

Formula I

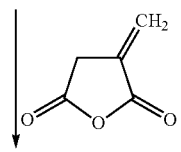

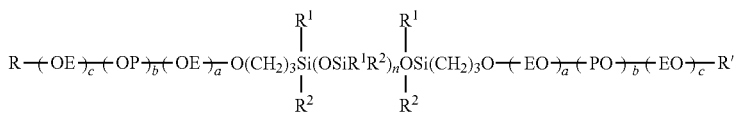

Formula III wherein R and R' independently represent hydrogen and a cyclic anhydride residue (half ester) represented by the formulae:

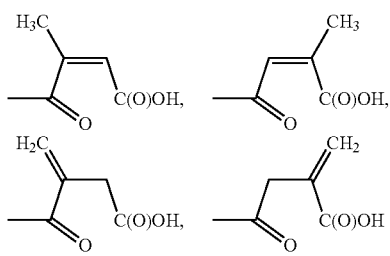

and all isomers thereof; subject to the proviso that R and R' can not both be hydrogen at the same time; and $R^1$, $R^2$, EO, PO, a, b, c, and n are as previously defined. The reaction product represented by Formula III will contain a mixture of dimethicone copolyol citraconates and itaconates including the regio- and stereo isomers thereof (isomers).

An exemplary reaction scheme illustrating the esterification of a dimethicone copolyol of Formula II is as follows:

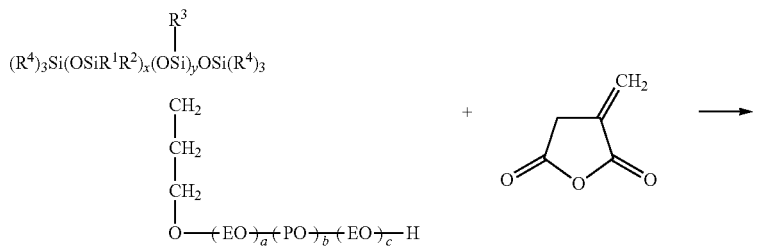

Formula II

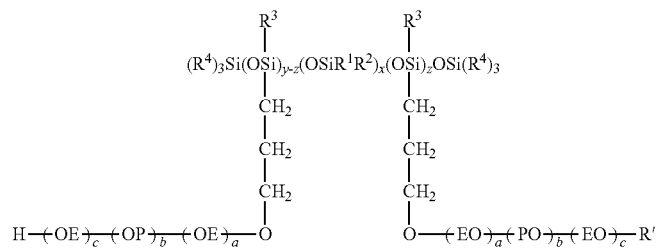

Formula IV wherein R' is a cyclic anhydride residue as previously defined, and, $R^1$, $R^2$, $R^3$, $R^4$, a, b, c, x and y are as previously defined, and z is ≤y. The reaction product represented by Formula IV will contain a mixture of dimethicone copolyol citraconates (in major portion) and itaconates (in minor portion) including the isomers thereof.

Surprisingly, it has been discovered that the dimethicone copolyol citraconates of Formulae III and IV wherein the R and R' groups contain olefinic unsaturation are readily polymerizable. It has also been found that the half esters formed from dimethicone copolyols and maleic anhydride are also polymerizable with a variety of copolymerizable monomers.

In one embodiment of the present invention the polymerizable dimethicone copolyol macromers conform to the following structures:

bond. The macromers of this invention can be employed in the synthesis of polymers to convey properties inherent to dimethicone copolyols to a particular polymer backbone. Such polymers can be used in personal care, textile and industrial formulations to deliver softness, lubricity, sensory, fixative, conditioning, water repellency, gloss, surface, and solubility properties, to name a few.

In one embodiment, the polymers of the invention can be polymerized from a monomer mixture comprising (on a total monomer weight basis): (a) about 0.1 to 100 weight percent of at least one dimethicone copolyol macromer selected from Formulae III, IIIa, IV and IVa above; (b) 0 to 99.9 weight percent of a non-ionic monomer; (c) 0 to 99.9 weight percent of at least an acidic vinyl monomer; (d) 0 to 99.9 weight percent of at least one cationic vinyl monomer; (e) 0 to 99.9

Formula IIIa

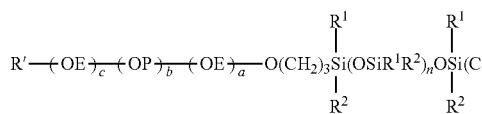 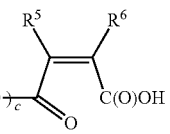

Formula IVa

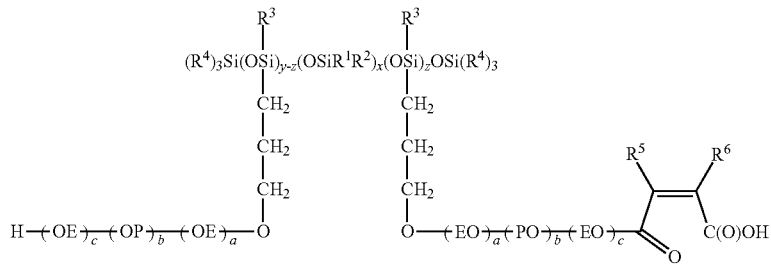

wherein $R^1$, $R^2$, $R^3$, $R^4$, EO (OE), PO(OP), a, b, c, n, x, y and z are as previously defined; $R^5$ and $R^6$ are independently selected from hydrogen and methyl, subject to the proviso that $R^5$ and $R^6$ can not both represent methyl at the same time; and R' represents hydrogen or a radical represented by the structure:

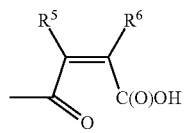

wherein $R^5$ and $R^6$ are defined as above. In one embodiment at least one of $R^5$ and $R^6$ in the formulae above is methyl.

In one embodiment of the invention, the dimethicone copolyol macromers set forth under Formulae III, IIIa, IV, and IVa are free radically polymerizable. The copolyol macromers are homopolymerizable and can be employed as building blocks to create a star-like, comb-like, brush-like, and/or flower-like polymers) or are copolymerizable and can be utilized as building blocks to design well-defined structure like arms, branches, rakes, combs graft copolymers) with ethylenically unsaturated free radically polymerizable monomers. By ethylenically unsaturated is meant that the monomer possesses at least one polymerizable carbon-carbon double weight percent of at least one associative vinyl monomer; (f) 0 to 99.9 weight percent of at least one semihydrophobic vinyl monomer; and (g) 0 to 5 weight percent of a crosslinking monomer. The amount and selection of each monomer employed in the polymerizable monomer mixture will depend on the desired properties of the polymer product. Suitable monomers that are copolymerizable with the dimethicone copolyol macromers are described below. While overlapping weight ranges for the various monomer components that make up the polymerizable monomer mixture have been expressed for selected embodiments of the invention, it should be readily apparent that the specific amount of each monomer component in the monomer mixture will be selected from its disclosed range such that the desired amount of each monomer will be adjusted so that the sum of all monomer components in the polymerizable monomer mixture will total 100 weight percent.

The polymers can optionally be prepared from a monomer mixture comprising one or more chain transfer agents, which are well known in the polymer arts.

The terms "halogen-substituted", "hydroxy-substituted", "carboxy-substituted", "polyoxyalkylene-substituted", alkyl-substituted", and "aryl-substituted" as used herein in reference to alkyl or aryl groups, and the like, mean that at least one hydrogen atom on an alkyl, aryl, or like group has been replaced by at least one halogen atom, hydroxyl group, carboxyl group, polyoxyalkylene group, alkyl group, or aryl group, respectively. As used herein, the terms "(meth)acrylic" acid, "(meth)acrylate", and "(meth)acrylamide" are meant to include the corresponding methyl derivatives of acrylic acid, alkyl acrylate, and acrylamide. For example, "(meth)acrylic" acid refers to acrylic acid and/or methacrylic acid, "(meth)acrylate" refers to alkyl acrylate and/or alkyl methacrylate, and "(meth)acrylamide" refers to acrylamide and/or methacrylamide derivatives.

Nonionic Vinyl Monomer

Nonionic vinyl monomers suitable for use in the present invention are copolymerizable, nonionic, ethylenically unsaturated monomers, which are well known in the art. In one embodiment the nonionic monomers are compounds having either of the following Formulae:

$$CH_2=C(X)Z, \quad (V)$$

$$CH_2=CH-OC(O)R^7; \quad (VI)$$

wherein, in each of formulas (V) and (VI), X is H or methyl; and Z is $-C(O)OR^8$, $-C(O)NH_2$, $-C(O)NHR^8$, $-C(O)N(R^8)_2$, $-C_6H_4R^8$, $-C_6H_4OR^8$, $-C_6H_4Cl$, $-C_6H_{11}$, $-C_6H_7(R^8)(R^8)(R^8)$ (e.g., tri-substituted cyclohexyl), $-CN$, $-NHC(O)CH_3$, $-NHC(O)H$, N-(2-pyrrolidonyl), N-caprolactamyl, $-C(O)NHC(CH_3)_3$, $-C(O)NHCH_2CH_2-N$-ethyleneurea, $-Si(R^7)_3$, $-C(O)O(CH_2)_xSi(R^7)_3$, $-C(O)NH(CH_2)_xSi(R^7)_3$, or $-(CH_2)_xSi(R^7)_3$; x is an integer in the range of 1 to about 6; each $R^7$ is independently linear and branched $C_1$ to $C_{18}$ alkyl; each $R^8$ is independently linear and branched $C_1$ to $C_{30}$ alkyl, hydroxy-substituted $C_2$ to $C_{30}$ alkyl, or halogen-substituted $C_1$ to $C_{30}$ alkyl.

Non limiting examples of suitable nonionic monomers include $C_1$ to $C_{30}$ alkyl(meth)acrylates; cyclohexyl(meth)acrylates; 3,3,5-trimethylcyclohexyl(meth)acrylates (TM-CHMA); $C_1$ to $C_{30}$ alkyl(meth)acrylamides; styrene; substituted styrenes, such as vinyl toluene (e.g., 2-methyl styrene), butyl styrene, isopropyl styrene, p-chloro styrene, and the like; vinyl esters, such as vinyl acetate, vinyl butyrate, vinyl caprolate, vinyl pivalate, vinyl neodecanoate, and the like; unsaturated nitriles, such as methacrylonitrile, acrylonitrile, and the like; and unsaturated silanes, such as trimethylvinylsilane, dimethylethylvinylsilane, allyldimethylphenylsilane, allyltrimethylsilane, 3-acrylamidopropyltrimethylsilane, 3-trimethylsilylpropyl(meth)acrylate, and the like. Non limiting examples of suitable water soluble nonionic monomers are $C_1$ to $C_6$ hydroxyalkyl(meth)acrylates, such as 2-hydroxyethyl(meth)acrylate (HEMA), 2-hydroxyethyl(meth)acrylate (2-HEA), 3-hydroxypropyl(meth)acrylate; glycerol mono(meth)acrylate; tris(hydroxymethyl)ethane mono(meth)acrylate; pentaerythritol mono(meth)acrylate; N-hydroxymethyl(meth)acrylamide; 2-hydroxyethyl(meth)acrylamide; 3-hydroxypropyl(meth)acrylamide; (meth)acrylamide; t-octyl(meth)acrylamide; N-(2,3-dihydroxypropyl)acrylamide; t-butyl(meth)acrylamide; N-vinyl caprolactam; N-vinyl pyrrolidone; methacrylamidoethyl-N-ethyleneurea (e.g., $CH_2=C(CH_3)C(O)NHCH_2CH_2-N$-ethyleneurea), $C_1$ to $C_4$ alkoxy-substituted (meth)acrylates and (meth)acrylamides, such as methoxyethyl(meth)acrylate, 2-(2-ethoxyethoxy)ethyl (meth)acrylate, and the like; and combinations thereof.

Other useful nonionic vinyl monomers include allyl alcohol, glycerol monoallyl ether, 3-methyl-3-buten-1-ol, and vinyl alcohol precursors and equivalents, such as vinyl acetate.

Acidic Vinyl Monomer

The acidic vinyl monomers suitable for use in the present invention are acidic, polymerizable, ethylenically unsaturated monomers preferably containing at least one carboxylic acid, sulfonic acid group, or a phosphonic acid group to provide an acidic or anionic functional site. These acid groups can be derived from monoacids or diacids, anhydrides of dicarboxylic acids, monoesters of diacids, and salts thereof.

Suitable acidic vinyl carboxylic acid-containing monomers include, but are not limited to acrylic acid, methacrylic acid, itaconic acid, citraconic acid, maleic acid, fumaric acid, crotonic acid, aconitic acid, and the like, and $C_1$ to $C_{18}$ alkylmonoesters of maleic, fumaric, itaconic, or aconitic acid, such as methyl hydrogen maleate, monoisopropyl maleate, butyl hydrogen fumarate, and the like. Anhydrides of dicarboxylic acids, such as maleic anhydride, itaconic anhydride, citraconic anhydride, and the like can also be utilized as acidic vinyl monomers. Such anhydrides generally hydrolyze to the corresponding diacids upon prolonged exposure to water, or at elevated pH.

Suitable sulfonic acid group-containing monomers include, but are not limited to vinyl sulfonic acid, 2-sulfoethyl methacrylate, styrene sulfonic acid, 2-acrylamido-2-methyl-propane sulfonic acid (AMPS), allyloxybenzene sulfonic acid, and the like. Particularly preferred are the sodium salt of styrene sulfonic acid (SSSA) and AMPS.

Non limiting examples of suitable phosphonic acid group-containing monomers include vinyl phosphonic acid, allyl phosphonic acid, 3-acrylamidopropyl phosphonic acid, and the like.

Suitable salts include, without limitation thereto, alkali metal salts, such as sodium, potassium and lithium salts; alkaline earth metal salts, such as calcium and magnesium salts; ammonium salts; and alkyl-substituted ammonium salts, such as salts of 2-amino-2-methyl-1-propanol (AMP), ethanolamine, diethanolamine, triethanolamine, triethylamine, and the like.

The foregoing monomers or salts thereof can be used as the acidic vinyl monomer component in mixtures of two or more.

Cationic Vinyl Monomer

Cationic vinyl monomers suitable for copolymerization are basic, polymerizable, ethylenically unsaturated monomers preferably containing at least one amino functional group. These basic amino groups can be derived from mono-, di- or poly-amino alkyl groups or nitrogen containing heteroaromatic groups. The amino group can comprise primary, secondary or tertiary amines. The monomers can be used in the amino form or in the salt form, as desired.

Non limiting examples of suitable cationic monomers can be selected from: a mono-($C_1$ to $C_4$)alkylamino($C_1$ to $C_8$)alkyl(meth)acrylate, a di-($C_1$ to $C_4$)alkylamino($C_1$ to $C_8$)alkyl(meth)acrylate, a mono-($C_1$ to $C_4$)alkylamino($C_1$ to $C_8$)alkyl(meth)acrylamide, a di-($C_1$ to $C_4$)alkylamino($C_1$ to $C_8$)alkyl(meth)acrylamide, a nitrogen-containing heterocyclic (meth)acrylamide, a nitrogen-containing heterocyclic (meth)acrylate, and mixtures thereof.

Specific examples of suitable cationic monomers include, but are not limited to 2-(N,N-dimethylamino)ethyl (meth)acrylate (DMAEMA), 3-(N,N-dimethylamino)propyl(meth)acrylate, 4-(N,N-dimethylamino)butyl (meth)acrylate, (N,N-dimethylamino)-t-butyl(meth)acrylate, 2-(tert-butylamino)ethyl(meth)acrylate (TBAEMA), 2-(N,N-diethylamino)ethyl (meth)acrylate (DEAEMA), 3-(N,N-diethylamino)propyl(meth)acrylate, 2-(N,N-dimethylamino)neopentyl (meth)acrylate (DMANPA), 4-(N,N-diethylamino)butyl (meth)acrylate, 2-(N,N-dipropylamino)ethyl (meth)acrylate, 3-(N,N-dipropylamino)propyl(meth)acrylate, 4-(N,N-dipropylamino)butyl (meth)acrylate, 3-(N,N-dimethylamino)propyl (meth)acrylate, 2-(4-morpholinyl)ethyl(meth)acrylate, 2-(4-morpholinyl)ethyl acrylate, N'-(2-N,N-dimethylamino)ethyl(meth)acrylamide, 2-(N,N-dimethylamino)propyl (meth)acrylamide (DMAPMAm), N'-(3-N,N-dimethylamino)propyl(meth)acrylamide, N-(2-pyridyl) (meth)acrylamide, N-(2-imidazoyl)(meth)acrylamide, N-(4-morpholinyl) (meth)acrylamide, N-(4-morpholinyl)(meth)acrylamide, 2-vinyl pyridine, 4-vinyl pyridine, N-vinyl-2-methylimidazole, N-vinylimidazole, N-vinyl-4-methylimidazole, and N-vinyloxazolidone, and mixtures thereof.

Suitable salt forms of the cationic monomers include, but are not limited to, mineral acid salts such as the hydrochloride, sulfate, $C_1$ to $C_{30}$ alkyl sulfate and phosphate salts; and organic acid salts such as the acetate, maleate, and fumarate salts; and the like.

Non limiting examples of salt forms of the cationic monomers include, but are not limited to, 3-trimethylammonium propyl(meth)acrylamide chloride, 3-trimethylammonium propyl acrylamide chloride, quaternized N,N-dimethylaminoethyl(meth)acrylate using $C_1$ to $C_{30}$ alkyl sulphate, quaternized N,N-dimethylaminoethyl methacrylate using methylchloride, quaternized vinyl imidazole, methacryloyl ethyl betaine, and methacryloyl N-oxide.

Associative Vinyl Monomer

Associative vinyl monomers (hydrophobic monomer) suitable for use in the synthesis of the polymers are compounds having an ethylenically unsaturated end group portion (i) for addition polymerization with the other monomers of the mixture; a polyoxyalkylene midsection portion (ii) for imparting selective hydrophilic properties to the product polymer and a hydrophobic end group portion (iii) for providing selective hydrophobic properties to the polymer.

The portion (i) supplying the ethylenically unsaturated end group preferably is derived from an ethylenically unsaturated mono or di-carboxylic acid or the anhydride thereof, more preferably a $C_3$ or $C_4$ mono- or di-carboxylic acid or the anhydride thereof. Alternatively, portion (i) of the associative monomer can be derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The midsection portion (ii) is preferably a polyoxyalkylene segment of about 5 to about 250, more preferably about 10 to about 120, and most preferably about 15 to about 60 repeating $C_2$ to $C_7$ alkylene oxide units. Preferred midsection portions (ii) include polyoxyethylene, polyoxypropylene, and polyoxybutylene segments comprising about 5 to about 150, more preferably about 10 to about 100, and most preferably about 15 to about 60 ethylene, propylene or butylene oxide units, and random or non-random sequences of ethylene oxide, propylene oxide and or butylene oxide units.

The hydrophobic end group portion (iii) of the associative monomers is preferably a hydrocarbon moiety belonging to one of the following hydrocarbon classes: a $C_8$ to $C_{40}$ linear alkyl, an aryl-substituted $C_2$ to $C_{40}$ alkyl, a $C_2$ to $C_{40}$ alkyl-substituted phenyl, a $C_8$ to $C_{40}$ branched alkyl, a $C_8$ to $C_{40}$ carbocyclic alkyl; and a $C_8$ to $C_{80}$ complex ester. Complex esters are formed by the esterification of a polyol with a long chained hydroxy acid which contains both a hydroxyl group and a carboxylic group. The carboxylic group of the long chained hydroxy acid reacts with at least one hydroxyl group of the polyol. In turn the hydroxyl group of the long chained hydroxy acid reacts with a carboxylic group of another long chained hydroxy acid and/or another long chained carboxylic acid. By long chained is meant that the hydroxy acid and the carboxylic acid contain from about 10 to 30 carbon atoms. The carbon chain can be saturated or unsaturated. Exemplary non-limiting examples of a suitable polyol are glycerol, sorbitol, pentaerythritol, trimethylol propane. An exemplary non-limiting example of a hydroxy acid is 12-hydroxy steric acid. Exemplary non-limiting long chain carboxylic acids are those that are the fatty acids derived from the vegetable oils and fatty acids set forth herein.

Non limiting examples of suitable hydrophobic end group portions (iii) of the associative monomers are linear or branched alkyl groups having about 8 to about 40 carbon atoms such as capryl ($C_8$), isooctyl (branched $C_8$), decyl ($C_{10}$), lauryl ($C_{12}$), myristyl ($C_{14}$), cetyl ($C_{16}$), cetearyl ($C_{16}$ to CO, stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), lacceryl ($C_{32}$), and the like.

Examples of linear and branched alkyl groups having about 8 to about 40 carbon atoms that are derived from a natural source include, without being limited thereto, alkyl groups derived from hydrogenated peanut oil, soybean oil and canola oil (all predominately $C_{18}$), hydrogenated tallow oil ($C_{16}$ to $C_{18}$), and the like; and hydrogenated $C_{10}$ to $C_{30}$ terpenols, such as hydrogenated geraniol (branched $C_{10}$), hydrogenated farnesol (branched $C_{15}$), hydrogenated phytol (branched $C_{20}$), and the like.

Non limiting examples of suitable $C_2$ to $C_{40}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Suitable $C_8$ to $C_{40}$ carbocylic alkyl groups include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials such as pinene, hydrogenated retinol, camphor, isobornyl alcohol, and the like.

Exemplary aryl-substituted $C_2$ to $C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non limiting examples of suitable $C_8$ to $C_{80}$ complex esters include hydrogenated castor oil (predominately the triglyceride of 12-hydroxystearic acid); 1,2-diacyl glycerols such as 1,2-distearyl glycerol, 1,2-dipalmityl glycerol, 1,2-dimyristyl glycerol, and the like; di-, tri-, or poly-esters of sugars such as 3,4,6-tristearyl glucose, 2,3-dilauryl fructose, and the like; and sorbitan esters such as those disclosed in U.S. Pat. No. 4,600,761 to Ruffner et al., the pertinent disclosures of which are incorporated herein by reference.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

Examples of associative vinyl monomers include those represented by the following Formula (VII):

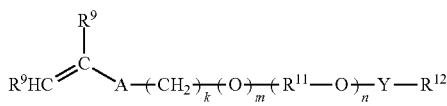

wherein, each $R^9$ is independently H, $C_1$ to $C_{30}$ alkyl, —C(O)OH, or —C(O)$OR^{10}$; $R^{10}$ is $C_1$ to $C_{30}$ alkyl; A is —$CH_2$C(O)O—, —C(O)O—, —O—, —$CH_2$O—, —NHC(O)NH—, —C(O)NH—, —Ar—$(CE_2)_z$-NHC(O)O—, —Ar—$(CE_2)_z$-NHC(O)NH—, or —$CH_2CH_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; $(R^{11}—O)_n$ is a polyoxyalkylene, which is a homopolymer, a random copolymer, or a block copolymer of $C_2$ to $C_4$ oxyalkylene units, wherein $R^{11}$ is $C_2H_4$, $C_3H_6$ (and isomers), $C_4H_8$, or a mixture thereof, and n is an integer in the range of about 5 to about 250, preferably about 5 to about 100, more preferably about 10 to about 80, and most preferably about 15 to about 60; Y is —$R^{11}$O—, —$R^{11}$NH—, —O(O)—, —C(O)NH—, —$R^{11}$NHC(O)NH—, or —C(O)NHC(O)—; and $R^{12}$ is a substituted or unsubstituted alkyl selected from the group consisting of a $C_8$ to $C_{40}$ linear alkyl, a $C_8$ to $C_{40}$ branched alkyl, a $C_8$ to $C_{40}$ carbocyclic alkyl, a $C_2$ to $C_{40}$ alkyl-substituted phenyl, an aryl-substituted $C_2$ to $C_{40}$ alkyl, and a $C_8$ to $C_{80}$ complex ester; wherein the $R^{11}$ alkylene and the $R^{12}$ alkyl group optionally includes one or more substituents selected from a hydroxyl group, a $C_1$ to $C_5$ alkoxyl group, and a halogen group.

Specific examples of associative vinyl monomers of Formula (VII) include cetyl polyethoxylated methacrylate (OEM), cetearyl polyethoxylated methacrylate (CSEM), stearyl polyethoxylated (meth)acrylate, arachidyl polyethoxylated (meth)acrylate, behenyl polyethoxylated (meth)acrylate (BEM), lauryl polyethoxylated methacrylate (LEM), cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated (meth)acrylate (TEM), hydrogenated castor oil polyethoxylated (meth)acrylate (HCOEM), canola polyethoxylated (meth)acrylate, and cholesterol polyethoxylated (meth)acrylate (CHEM), where the polyethoxylated portion of the monomer comprises about 5 to about 100, preferably about 10 to about 80, and more preferably about 15 to about 60 ethylene oxide repeating units.

Semihydrophobic Vinyl Monomer

As used herein the term semihydrophobic vinyl monomer refers to compounds having two portions: (i) an ethylenically unsaturated end group moiety for addition polymerization with the other monomers of the reaction mixture, and (ii) a polyoxyalkylene moiety for attenuating the associations between the hydrophobic groups of the polymer or hydrophobic groups from other materials in a composition containing the polymer. A semihydrophobic vinyl monomer is similar in structure to the associative vinyl monomer set forth above, but has a substantially non-hydrophobic end group component and thus, does not impart any associative properties to the polymer.

In one aspect, the unsaturated end group portion (i) supplying the vinyl or other ethylenically unsaturated end group for addition polymerization can be derived from an ethylenically unsaturated mono- or di-carboxylic acid or the anhydride thereof, such as, for example, a $C_3$ or $C_4$ mono- or di-carboxylic acid, or the anhydride thereof. Alternatively, in another aspect, the end group portion (i) can be derived from an allyl ether, vinyl ether or a nonionic unsaturated urethane.

The polymerizable unsaturated end group portion (i) can also be derived from a $C_8$ to $C_{30}$ unsaturated fatty acid group containing at least one free carboxy-functional group. This $C_8$ to $C_{30}$ group is part of the unsaturated end group portion (i) and is different from the hydrophobic groups pendant to the associative monomers, which are specifically separated from the unsaturated end group of the associative monomer by a hydrophilic "spacer" portion.

The polyoxyalkylene portion (ii) specifically comprises a long-chain polyoxyalkylene segment, which is substantially similar to the hydrophilic portion of the associative monomers. Preferred polyoxyalkylene portion (ii) includes polyoxyethylene, polyoxypropylene, and polyoxybutylene units comprising about 5 to about 250, and preferably about 10 to about 100 oxyalkylene units. When the semihydrophobic vinyl monomer comprises more than one type of oxyalkylene unit, the units can be arranged in random, non-random, or block sequences.

In one embodiment, exemplary semihydrophobic vinyl monomers include at least one compound represented by one of the following formulae (VIII) or (IX):

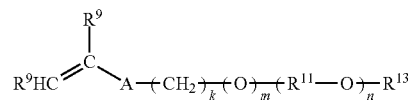

Formula VIII

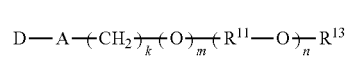

Formula IX wherein in each of Formulae VIII and IX $R^9$, $R^{11}$, A, k, m, and n are as described previously; D is a $C_8$ to $C_{30}$ unsaturated alkyl, or a carboxy-substituted $C_8$ to $C_{30}$ unsaturated alkyl; and $R^{13}$ is H or $C_1$ to $C_4$ alkyl.

In one embodiment, the semihydrophobic vinyl monomers include monomers having the following formulae:

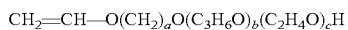

or

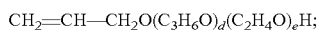

wherein a is an integer of 2, 3, or 4; b is an integer in the range of 1 to about 10 in one aspect, 2 to about 8 in another aspect, and about 3 to about 7 in a further aspect; c is an integer in the range of about 5 to about 50 in one aspect, about 8 to about 40 in another aspect, and about 10 to about 30 in a further aspect; d is an integer in the range of 1 to about 10 in one aspect, about 2 to about 8 in another aspect, and about 3 to about 7 in a further aspect; and e is an integer in the range of about 5 to about 50 in one aspect, and about 8 to about 40 in another aspect.

Exemplary examples of semihydrophobic vinyl monomers include polymerizable emulsifiers commercially available under the trade names EMULSOGEN® R109, R208, R307, RAL109, RAL208, and RAL307 sold by Clariant Corporation; BX-AA-E5P5 sold by Bimax, Inc.; and MAXEMUL® 5010 and 5011 sold by Uniqema; and combinations thereof. Particularly preferred SVS monomers include EMULSOGEN® R208, R307, and RAL307.

According to the manufacturers EMULSOGEN® R109 is a randomly ethoxylated/propoxylated 1,4-butanediol vinyl ether having the empirical formula $CH_2=CH-O(CH_2)_4O(C_3H_6O)_4(C_2H_4O)_{10}H$; EMULSOGEN® R208 is a randomly ethoxylated/propoxylated 1,4-butanediol vinyl ether having the empirical formula: $CH_2=CH-O(CH_2)_4O(C_3H_6O)_4(C_2H_4O)_{20}H$; EMULSOGEN® R307 is a randomly ethoxylated/propoxylated 1,4-butanediol vinyl ether having the empirical formula: $H_2=CH-O(CH_2)_4O(C_3H_6O)_4(C_2H_4O)_{30}H$; EMULSOGEN® RAL109 is a randomly ethoxylated/propoxylated allyl ether having the empirical formula $CH_2=CHCH_2O(C_3H_6O)_4(C_2H_4O)_{10}H$; EMULSOGEN® RAL208 is a randomly ethoxylated/propoxylated allyl ether having the empirical formula $CH_2=CHCH_2O(C_3H_6O)_4(C_2H_4O)_{20}H$; EMULSOGEN® RAL307 is a randomly ethoxylated/propoxylated allyl ether having the empirical formula $CH_2=CHCH_2O(C_3H_6O)_4(C_2H_4O)_{30}H$; MAXEMUL® 5010 is a carboxy-functional $C_{12}$ to $C_{15}$ alkenyl hydrophobe, ethoxylated with about 24 ethylene oxide units; MAXEMUL® 5011 is a carboxy-functional $C_{12}$ to $C_{15}$ alkenyl hydrophobe, ethoxylated with about 34 ethylene oxide units; and BX-AA-E5P5 is a randomly ethoxylated/propoxylated allyl ether having the empirical formula $CH_2=CHCH_2O(C_3H_6O)_5(C_2H_4O)_5H$.

Crosslinking Monomer

The polymers of the present invention can be prepared from a monomer mixture comprising one or more crosslinking monomers for introducing branching and controlling molecular weight. Suitable polyunsaturated crosslinkers are well known in the art. Mono-unsaturated compounds carrying a reactive group that is capable of causing a formed copolymer to be crosslinked before, during, or after polymerization has taken place can also be utilized. Other useful crosslinking monomers include polyfunctional monomers containing multiple reactive groups such as epoxide groups, isocyanate groups, and hydrolyzable silane groups. Various polyunsaturated compounds can be utilized to generate either a partially or substantially cross-linked three dimensional network.

Examples of suitable polyunsaturated crosslinking monomer components include, without being limited thereto, polyunsaturated aromatic monomers such as divinylbenzene, divinyl naphthylene, and trivinylbenzene; polyunsaturated alicyclic monomers, such as 1,2,4-trivinylcyclohexane; difunctional esters of phthalic acid such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers include polyalkenyl ethers such as triallyl pentaerythritol, diallyl pentaerythritol, diallyl sucrose, octaallyl sucrose, and trimethylolpropane diallyl ether; polyunsaturated esters of polyalcohols or polyacids such as 1,6-hexanediol di(meth) acrylate, tetramethylene tri(meth)acrylate, allyl acrylate, diallyl itaconate, diallyl fumarate, diallyl maleate, trimethylolpropane tri(meth)acrylate, trimethylolpropane di(meth) acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, and triethyleneglycol di(meth)acrylate; polyunsaturated silanes, such as dimethyldivinylsilane, methyltrivinylsilane, allyldimethylvinylsilane, diallyldimethylsilane, and tetravinylsilane; polyunsaturated stannanes, such as tetraallyl tin, and diallyldimethyl tin; and the like.

Useful monounsaturated compounds carrying a reactive group include N-methylolacrylamide; N-alkoxy(meth)acrylamide, wherein the alkoxy group is a $C_1$ to $C_{18}$ alkoxy; and unsaturated hydrolyzable silanes such as triethoxyvinylsilane, tris-isopropoxyvinylsilane, and 3-triethoxysilylpropyl methacrylate; and the like.

Useful polyfunctional crosslinking monomers containing multiple reactive groups include, but are not limited to, hydrolyzable silanes such as ethyltriethoxysilane and ethyltrimethoxysilane; epoxy-substituted hydrolyzable silanes, such as 2-(3,4-epoxycyclohexyl)ethyltriethoxysilane and 3-glycidoxypropyltrimethyoxysilane; polyisocyanates, such as 1,4-diisocyanatobutane, 1,6-diisocyanatohexane, 1,4-phenylenediisocyanate, and 4,4'-oxybis(phenylisocyanate); unsaturated epoxides, such as glycidyl(meth)acrylate and allylglycidyl ether; polyepoxides, such as diglycidyl ether, 1,2,5,6-diepoxyhexane, and ethyleneglycoldiglycidyl ether; and the like.

Particularly useful are polyunsaturated crosslinkers derived from ethoxylated polyols, such as diols, triols and bis-phenols, ethoxylated with about 2 to about 100 moles of ethylene oxide per mole of hydroxyl functional group and end-capped with a polymerizable unsaturated group such as a vinyl ether, allyl ether, acrylate ester, methacrylate ester, and the like. Examples of such crosslinkers include bisphenol A ethoxylated di(meth)acrylate; bisphenol F ethoxylated di(meth)acrylate, ethoxylated trimethylol propane tri(meth) acrylate, and the like. Other ethoxylated crosslinkers useful in the polymers of the present invention include ethoxylated polyol-derived crosslinkers disclosed in U.S. Pat. No. 6,140,435 to Zanotti-Russo, the pertinent disclosures of which are incorporated herein by reference.

Non limiting examples of crosslinking monomers are acrylate and methacrylate esters of polyols having at least two acrylate or methacrylate ester groups, such as trimethylolpropane triacrylate (TMPTA), trimethylolpropane ethoxylated (15) triacrylate (TMPEO15TA), trimethylolpropane dimethacrylate, triethylene glycol dimethacrylate (TEGDMA), ethoxylated (30) bisphenol A dimethacrylate (EOBDMA), and the like.

Chain Transfer Agent

Suitable chain transfer agents (CTAs) for use in this invention, without being limited thereto, are selected from a variety of thio and disulfide containing compounds, such as $C_1$ to $C_{18}$ alkyl mercaptans, mercaptocarboxylic acids, mercaptocarboxylic esters, thioesters, $C_1$ to $C_{18}$ alkyl disulfides, aryldisulfides, polyfunctional thiols, and the like; phosphites and hypophosphites; haloalkyl compounds, such as carbon tetrachloride, bromotrichloromethane, and the like; and unsaturated chain transfer agents, such as alpha-methylstyrene.

Polyfunctional thiols include trifunctional thiols, such as trimethylolpropane-tris-(3-mercaptopropionate), tetrafunctional thiols, such as pentaerythritol-tetra-(3-mercaptopropionate), pentaerythritol-tetra-(thioglycolate), and pentaerythritol-tetra-(thiolactate); hexafunctional thiols, such as dipentaerythritol-hexa-(thioglycolate); and the like.

Alternatively, the chain transfer agent can be any catalytic chain transfer agent which reduces molecular weight of addition polymers during free radical polymerization of vinyl monomers. Examples of catalytic chain transfer agents include, for example, cobalt complexes (e.g., cobalt (II) chelates). Catalytic chain transfer agents can often be utilized in relatively low concentrations relative to thiol-based CTAs.

In one embodiment of the invention the chain transfer agents include octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, dodecyl thioglycolate, and the like. The chain transfer agents can be added to a monomer reaction mixture preferably in amounts of up to about 10 weight percent of polymerizable monomer mixture, based on total monomer mixture weight. In one embodiment, the chain transfer agent is present in an amount of at least about 0.01 percent by weight based on the total monomer weight.

The dimethicone copolyol macromer of the present invention can be polymerized alone or in combination with at least one of copolymerizable monomers (b) through (g). The polymerization can be conducted in the optional presence of a chain transfer agent. The unsaturated monomers can be polymerized by a variety of well known free radical polymerization techniques such as bulk polymerization, photo polymerization, microwave polymerization, solution polymerization, precipitation polymerization, suspension polymerization, emulsion polymerization, inverse emulsion polymerization, microemulsion polymerization and the like.

Initiators which can be used for the free radical polymerization processes of the invention are the water soluble and water insoluble persulfate, peroxide, organic hydroperoxides, organic peracids, and azo compounds. Suitable initiators include but are not limited to the ammonium persulfate, potassium persulfate, sodium persulfate, hydrogen peroxide, dibenzoyl peroxide, benzoyl peroxide, acetyl peroxide, lauryl peroxide, tert-butyl perpivalate, tert-butyl per-2-ethyl hexanoate, di-tert-butyl peroxide, di-(2-ethylhexyl)-peroxy dicarbonate, tert-butyl hydroperoxide, cumene hydroperoxide, azobisisobutyronitrile, azobis(2-amidinopropane)dihydrochloride or 2,2'-azobis(2-methyl-butyronitrile), peracetic acid. The peroxides and peracids can optionally be activated with reducing agents, such as sodium bisulfite or ascorbic acid, transition metals, hydrazine, and the like. Mixtures of initiator systems can also be utilized, such as, for example, sulfate/sodium peroxodisulfate, tert-butyl hydroperoxide/sodium sulfite, tert-butyl hydroperoxide/sodium hydroxymethanesulfinate. The initiators can be employed in suitable amounts, for example, in amounts of from 0.05 to 5% by weight, based on the amount of monomers to be polymerized.

In one embodiment of the invention, the polymers can be prepared using solution polymerization (e.g., precipitation polymerization) in a polar solvent or non-polar solvent and mixtures thereof. Exemplary solvents include but are not limited to water, methanol, methylene chloride chloroform, carbon tetrachloride, ethanol, isopropanol, hexane, cyclohexane, ethyl acetate, methylethyl ketone and benzene, toluene, N-methylpyrrolidone, and mixtures of these solvents. The amounts of monomers and solvents can be chosen to give from 15 to 90% by weight of monomer in solution (based on the total weight of monomer and solvent). The polymerization is usually carried out at temperatures of from 40 to 140° C. and at atmospheric pressure or under autogeneous pressure.

In another embodiment of the invention, the polymers can be synthesized via anionic and cationic emulsion polymerization techniques as is well known in the polymer art. Typically the anionic emulsion polymerization process is carried out at a reaction temperature in the range of about 30 to about 95° C., however, higher or lower temperatures can be used. To facilitate emulsification of the monomer mixture, the emulsion polymerization can be carried out in the presence of anionic surfactants, such as fatty alcohol sulfates or alkyl sulfonates, nonionic surfactants, such as linear or branched alcohol ethoxylates, amphoteric surfactants, or mixtures thereof. The emulsion polymerization reaction mixture also includes one or more free radical initiators in an amount in the range of about 0.01 to about 3 weight percent based on total monomer weight. The polymerization can be performed in an aqueous or aqueous alcohol medium at a low pH, i.e., preferably not more than about pH 4.5.

Anionic surfactants suitable for facilitating emulsion polymerizations are well known in the polymer art, and include but are not limited to sodium lauryl sulfate, sodium dodecyl benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like.

In a typical cationic polymerization procedure, a mixture of monomers is added with mixing agitation to a solution of emulsifying surfactant, such as a nonionic surfactant, preferably a linear or branched alcohol ethoxylate, or mixtures of nonionic surfactants and anionic surfactants, such as fatty alcohol sulfates or alkyl sulfonates, in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable free radical polymerization catalyst, as is well known in the emulsion polymerization art. The reaction is agitated until the polymerization is complete, typically for a time in the range of about 4 to about 16 hours. The monomer emulsion can be heated to a temperature in the range of about 20 to about 80° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use.

Nonionic surfactants suitable for facilitating cationic emulsion polymerizations are well known in the polymer art, and include, without limitation, linear or branched alcohol ethoxylates, $C_8$ to $C_{12}$ alkylphenol alkoxylates, such as octylphenol ethoxylates, polyoxyethylene polyoxypropylene block copolymers, and the like. Other useful nonionic surfactants include $C_8$ to $C_{22}$ fatty acid esters of polyoxyethylene glycol, mono and diglycerides, sorbitan esters and ethoxylated sorbitan esters, $C_8$ to $C_{22}$ fatty acid glycol esters, block copolymers of ethylene oxide and propylene oxide having an HLB value of greater than about 15, ethoxylated octylphenols, and combinations thereof.

In one aspect, alkylphenol alkoxylate surfactants include an octylphenol sold under the trade name IGEPAL® CA-897 by Rhodia, Inc. Preferred linear alcohol alkoxylates include polyethylene glycol ethers of cetearyl alcohol (a mixture of cetyl and stearyl alcohols) sold under the trade names PLURAFAC® C-17, PLURAFAC® A-38 and PLURAFAC® A-39 by BASF Corp. Preferred polyoxyethylene polyoxypropylene block copolymers include copolymers sold under the trade names PLURONIC® F127, and PLURONIC® L35 by BASF Corp.

In another aspect, the nonionic surfactants include Ethoxylated (50) linear fatty alcohols such as DISPONIL® A 5060 (Cognis), branched alkyl ethoxylates such as GENAPOL® X 1005 (Clariant Corp.), secondary $C_{12}$ to $C_{14}$ alcohol ethoxylates such as TERGITOL® S15-30 and S15-40 (Dow Chemical Co.), ethoxylated octylphenol-based surfactants such as TRITON® X-305, X-405 and X-705 (Dow Chemical Co.), IGEPAL® CA 407, 887, and 897 (Rhodia, Inc.), ICONOL® OP 3070 and 4070 (BASF Corp.), SYNPERONIC® OP 30 and 40 (Uniqema), block copolymers of ethylene oxide and propylene oxide such as PLURONIC® L35 and F127 (BASF Corp.), and secondary $C_{11}$ alcohol ethoxylates such as EMULSOGEN® EPN 407 (Clariant Corp.). Numerous other suppliers are found in the trade literature.

The free radical polymerization initiators discussed above are suitable herein. Exemplary commercially available polymerization initiators include the VAZO® free radical polymerization initiators, available from DuPont, such as VAZO® 44 (2,2'-azobis(2-(4,5-dihydroimidazolyl)propane), VAZO® 56 (2,2'-azobis(2-methylpropionamidine)dihydrochloride), and VAZO® 68 (4,4'-azobis(4-cyanovaleric acid).

Optionally, other emulsion polymerization additives, which are well known in the emulsion polymerization art, such as buffering agents, chelating agents, inorganic electrolytes, chain terminators, antifoaming agent, biocides diluents, and pH adjusting agents can be included in the polymerization system.

An exemplary general anionic emulsion polymerization procedure for the preparation of alkali swellable or alkali soluble polymer embodiment of the present invention is provided below:

A monomer emulsion is prepared in a first reactor equipped with a nitrogen inlet and an agitator, by combining a desired amount of each monomer in water containing an emulsifying amount of an anionic surfactant under a nitrogen atmosphere and with mixing agitation. To a second reactor equipped with an agitator, nitrogen inlet and feed pumps are added a desired amount of water and additional anionic surfactant, if desired, under a nitrogen atmosphere, and the contents of the second reactor are heated with mixing agitation. After the contents of the second reactor reach a temperature in the range of about 55 to 98° C., a free radical initiator is injected into the so formed aqueous surfactant solution in the second reactor, and the monomer emulsion from the first reactor is then gradually pumped into the second reactor over a period of typically in the range of about one to about four hours at a controlled reaction temperature in the range of about 45 to 95° C. After completion of the monomer addition, an additional quantity of free radical initiator can be added to the second reactor, if desired, and the resulting reaction mixture is typically held at a temperature of about 45 to 95° C. for a time period sufficient to complete the polymerization reaction. The resulting polymer emulsion can then be cooled and discharged from the reactor.

One skilled in the polymer arts will recognize that the amounts of each monomer component can be adjusted to obtain polymers having any desired ratio of monomers. Larger or smaller proportions of water may also be utilized, as desired. Water miscible solvents, such as alcohols, and other polymerization additives, as described above, may also be included in the reaction mixture. Nonionic surfactants, such as linear or branched alcohol ethoxylates, can also be added as is known in the emulsion polymerization art.

The product polymer emulsions can be prepared to preferably contain about 1 percent to about 60 percent total polymer solids, more preferably about 10 percent to about 50 percent total polymer solids, most preferably about 15 percent to about 45 percent total polymer solids (TS) based on the weight of the polymer.

Prior to any neutralization, the polymer emulsions, as produced, typically have a pH in the range of about 2 to not more than about 5.5, a Brookfield viscosity of not more than about 100 milli-Pascal seconds (mPa·s) at ambient room temperature (spindle #2, 20 rpm) and a glass transition temperature (Tg) of not more than about 250° C. as determined by Method below.

Optionally, the produced polymer emulsions can be further processed by adjusting the pH to a value preferably in the range of about 3 to about 7.5 or greater, if an alkaline pH is desired, with alkaline materials, preferably alkali metal hydroxides, organic bases, and the like. The polymer emulsions typically swell to a viscosity greater than about 100 mPa·s and form viscous solutions or gels at neutral to alkaline pH, and the polymers are generally substantially stable at such pH values, even at pH values greater than about 12. The polymer emulsions can be diluted with water or solvent, or concentrated by evaporation of a portion of the water. Alternatively, the obtained polymer emulsion may be substantially dried to a powder or crystalline form by utilizing equipment well known in the art, such as, for example, a spray drier, a drum drier, or a freeze drier.

The polymers/monomers of the present invention insofar as they contain ionizable groups can be fully or partially neutralized with acids or bases before or after polymerization to adjust the solubility or dispensability in aqueous medium. In addition, the viscosity properties of the polymers can be adjusted by neutralizing the polymer.

Non limiting examples of suitable neutralizing agents for monomers and polymers that carry anionic groups are mineral bases and organic bases. Non limiting examples of mineral bases include the alkali metal hydroxides (e.g., sodium and potassium); sodium carbonate; ammonium hydroxide; and ammonia. Non limiting examples of organic bases such as amino alcohols (e.g., 2-amino-2-methyl-1-propanol, monoethanolamine, diethanolamine, triethanolamine, triisopropylamine, tris[(2-hydroxy)-1-propyl]amine, 2-amino-2-methyl-1,3-propanediol, 2-amino-2-hydroxymethyl-1,3-propanediol; diamines such as lysine; cocamine; oleamine; and mopholine.

Non limiting examples of suitable neutralizing agents for monomers and polymers that carry cationic groups are organic acids, including amino acids, and inorganic mineral acids. Non limiting examples of organic acids include acetic acid, citric acid, fumaric acid, glutamic acid, tartaric acid, lactic acid, and glycolic acid. Non limiting examples of mineral acids include hydrochloric acid, nitric acid, phosphoric acid, sodium bisulfate, sulfuric acid, and the like, and mixtures thereof.

The polymers of the invention that contain anionic and/or cationic groups can swell upon neutralization with the appropriate base or acid. These polymers beneficially can thicken acidic or basic aqueous formulations to provide aesthetically smooth-textured products that flow smoothly and spread easily. The inventive, multi-purpose polymers can be employed as thickeners, emulsifiers, stabilizers, suspending agents, film formers, conditioners, moisturizers, spreading aids, surface modifiers, shine enhancers, and carriers for enhancing the efficacy, deposition or delivery of chemically and physiologically active ingredients and cosmetic materials, and as vehicles for improving the psychosensory, and aesthetic properties of a formulation in which they are included. The cationic character of the polymers at low pH makes them useful as antistatic agents, and, under certain conditions, may also provide biocidal, anti-microbial, or other preservative activity.

Advantageously, the polymers of this invention can be employed, without being limited thereto, in personal care products, health care products, household care products, institutional and industrial (collectively "I&I") care products, and the like. The polymers can be employed as a film forming conditioner, and for promoting the deposition of silicone, conditioning agents or aids, color cosmetics and of polar and non-polar oils on skin, hair, nails, and fibers. Further, the polymers can be employed in products for industrial chemical processes, textile finishing processes, printing, adhesive coating, and like applications as, for example, rheology modifiers, emulsifiers, stabilizers, solubilizers, suspending agents, flocculents, shine enhancers, surface modifiers, and pigment and grinding additives.

The following examples are presented for the purpose of illustrating the invention disclosed herein in greater detail. However, the examples are not to be construed as limiting the invention in any manner. Unless otherwise specified all parts are given by weight and the term "level" means weight percent.

Methods Description

Clarity

When reported, the clarity of the polymer-containing composition was measured in % T (transmittance) by Brinkmann PC 920 calorimeter at least about 24 hours after the composition was made. Clarity measurements were taken against deionized water (clarity rating of 100%). Compositions having a clarity of about 60% or more were substantially clear; compositions having a clarity in the range of about 45 to 59% were judged substantially translucent.

Glass Transition Temperature (Tg)

The glass transition temperature (Tg) of the inventive polymers is determined by well known Differential Scanning calorimetry (DSC) technique.

Turbidity

When reported, the turbidity of a polymer-containing composition was determined in Nephelometric Turbidity Units (NTU) employing a nephelometric turbidity meter with distilled water (NTU=0) as the standard. Compositions having an NTU value of about 90 or greater were judged turbid.

Viscosity

The reported viscosity of each polymer containing composition was measured in milli-Pascal seconds (mPa·s), employing a Brookfield rotating spindle viscometer, (Brookfield, Model RVT) at about 20 revolutions per minute (rpm), at ambient room temperature of about 20 to 25° C. (hereafter referred to as Brookfield viscosity). Viscosity was measured on freshly prepared compositions (referred to as "initial viscosity", and re-measured after allowing the composition to age for at least about 24 hours at ambient room temperature (referred to as "24-hour viscosity"). Where only one viscosity value is shown, the viscosity value is the 24-hour viscosity, unless otherwise indicated.

Yield Value

Yield Value, also referred to as Yield Stress, is herein defined as the initial resistance to flow under stress. It can be measured using a number of techniques, such as via the use of a constant stress rheometer or via extrapolation using a Brookfield viscometer. These techniques and the usefulness of the Yield Value measurement are further explained in Technical Data Sheet Number 244 available from Noveon, Inc., herein incorporated by reference.

Materials Abbreviations and Trade Names

AA acrylic acid
AAE5P5 a randomly ethoxylated-5/propoxylated-5 allyl ether (BX-AA-E5P5, Bimax, Inc.)
AMP-95 aminomethyl propanol
AMPS® monomer 2-acrylamido-2-methylpropane sulfonic acid
APE allylpentaerythritol
Bam t-butylacrylamide
BEM25 beheneth-25 methacrylate
Bruggolite® FF6 sodium hydroxymethane sulfinate dihydrate—reducing agent (Bruggeman Chemical U.S.)
CitA citraconic anhydride
CSEM25 ceteareth-25 methacrylate
DC 5103 pendant dimethicone copolyol (PEG-7 dimethicone), MW=2,500, CAS No. 68937-54-2, Dow Corning
DMAEMA N,N'-dimethylaminoethyl methacrylate
EA ethyl acrylate
EMULSOGEN® EPN 407 secondary $C_{11}$ ethoxylate having 40 ethylene oxide units per alcohol unit, Clariant Corp.)
IPA isopropyl alcohol
ItA itaconic anhydride
Luperox 11M 75 t-butyl peroxypivalate free radical initiator (75% solution in odorless mineral sprits), Atofina
MAA methacrylic acid
MalA maleic anhydride
MMA methyl methacrylate
Oam t-Octylacrylamide
RAL 307a randomly ethoxylated-30/propoxylated-5 allyl ether
Silsoft® 305 pendant dimethicone copolyol (PEG-5/PPG-3 methicone), MW=600, CAS No. 134180-76-0, GE Silicones/OSi Specialties
Silsoft® 475 pendant dimethicone copolyol (PEG-23/PPG-6 dimethicone), MW=19,000, CAS No. 68937-55-3, GE Silicones/OSi Specialties
Silsoft® 810 linear dimethicone copolyol (PEG-8 dimethicone), MW=1,700, CAS No. 102783-01-7, GE Silicones/OSi Specialties
Silsoft® 895 pendant dimethicone copolyol (PEG-17 dimethicone), MW=5,000, CAS No. 68937-54-2, GE Silicones/OSi Specialties
STY styrene
SucA succinic anhydride
TEGDMA triethylene glycol dimethacrylate
TMCHMA trimethyl cyclohexyl methacrylate (Ciba Specialty Chemicals)
TMPEO15TA trimethylolpropane PEG-15 triacrylate
TMPTA trimethylolpropane triacrylate
WAM II methacrylamidoethyl-N-ethylene urea, SIPOMER® WAM II, Rhodia, Inc.

EXAMPLES SM 1 to SM 11

A. Dimethicone Copolyol Macromer Synthesis (without Catalyst)

Dimethicone copolyol macromers (SM) containing terminal and pendant polyether groups conforming to Formulae III, IIIa, IV, and IVa are synthesized by reacting the cyclic anhydrides and the dimethicone copolyols set forth in Table 1A.

A 2 L glass reactor, equipped with a mechanical stirrer, nitrogen inlet, temperature probe connected to an electronic controller, and a water condenser is charged with the respective dimethicone copolyol (Table 1A). Under stirring the copolyol is heated to 80 to 105° C. and stripped under vacuum for 15 minutes to 1 hour. The reactor is cooled to 80 to 85° C., vacuum broken with $N_2$ and then the respective cyclic anhydride (Table 1A) is charged to the reactor. The stirred mixture is heated at 80 to 85° C. for 1 to 3 hours. The mixture is then stripped under vacuum for 15 minutes, vacuum broken with nitrogen, and cooled to 50° C. The mixture is then filtered to remove particulates. In each example, analysis by $^1$H NMR spectroscopy confirms formation of the respective dimethicone copolyol carboxylate half esters.

B. Dimethicone Copolyol Macromer Synthesis (with Catalyst)

Using a set up identical to the no catalyst synthesis procedure above, dimethicone copolyol and anhydrous alkali metal acetate (0.7 g, 0.2% w/w of total recipe components) are heated to 80° C. under vacuum for 15 minutes. Following backfilling with nitrogen, the mixture is allowed to react with the cyclic anhydride for 1 to 2 hours at 80 to 82° C. Analysis by $^1$H NMR spectroscopy confirms formation of the respective dimethicone copolyol carboxylate half ester (Table 1B).

TABLE 1A

Macromer Synthesis

| Ex. No. | Dimethicone Copolyol (DMC) | Amount of DMC (g) | Cyclic Anhydride (CA) | OH:CA (equivalents) | Amount of CA (g) |
|---|---|---|---|---|---|
| SM1 | Silsoft 305 | 299.6 | ItA | 1:1 | 54.8 |
| SM2 | Silsoft 810 | 299.7 | ItA | 1:1 | 45.8 |
| SM3 | Silsoft 810 | 300.0 | ItA | 1:0.5 | 23.1 |
| SM4 | Silsoft 810 | 300.0 | CitA | 1:1 | 46.1 |
| SM5 | DC 5103 | 672.1 | MalA | 1:0.75 | 77.9 |
| SM6 (comparative) | Silsoft 475 | 250.0 | SucA | 1:0.5 | 10.1 |
| SM7 | Silsoft 475 | 250.0 | MalA | 1:0.5 | 9.9 |
| SM8 | Silsoft 475 | 250 | ItA | 1:0.25 | 5.72 |
| SM9 | Silsoft 475 | 400 | ItA | 1:0.5 | 18.1 |
| SM9a[1] | Silsoft 475 | 335.9 | ItA | 1:0.5 | 13.4 |
| SM10 | Silsoft 475 | 238.0 | ItA | 1:0.75 | 16.1 |
| SM11 | Silsoft 895 | 470.9 | ItA | 1:0.5 | 29.1 |

[1]Catalyst: Anhydrous potassium acetate at 0.2% w/w of total recipe

TABLE 1B

Macromer Synthesis Product

| Ex. No | Formula | a | b | c | z | Anhydride Residue Source |
|---|---|---|---|---|---|---|
| SM1 | IV | 5 | 3 | 0 | z = y | ItA |
| SM2 | III | 8 | 0 | 0 | z = y | ItA |
| SM3 | III | 8 | 0 | 0 | z ≤ y | ItA |
| SM4 | III | 8 | 0 | 0 | z = y | CitA |
| SM5 | IVa | 7 | 0 | 0 | z ≤ y | MalA |
| SM6 | Comparative | 23 | 6 | 0 | z ≤ y | SucA |
| SM7 | IV | 23 | 6 | 0 | z ≤ y | MalA |
| SM8 | IV | 23 | 6 | 0 | z ≤ y | ItA |
| SM9 | IV | 23 | 6 | 0 | z ≤ y | ItA |
| SM9a | IV | 23 | 6 | 0 | z ≤ y | ItA |
| SM10 | IV | 23 | 6 | 0 | z ≤ y | ItA |
| SM11 | IV | 17 | 0 | 0 | z ≤ y | ItA |

Examples 1 and 2 illustrate the bulk homopolymerization of two olefinically unsaturated dimethicone copolyol macromers (SM) of the invention. One macromer is derived from a substituted cyclic anhydride (i.e., itaconic anhydride) and the other macromer is derived from an unsubstituted cyclic anhydride (i.e., maleic anhydride).

EXAMPLE I

A 100 ml three neck-round bottom flask with magnetic stirring, thermocouple is flushed with nitrogen. The flask is charged with 30 g of the dimethicone copolyol macromer of Example SM 11 (Table 1B). An ammonium persulfate initiator solution (2.6 g in 25 g water) is added in several portions at 4 hour intervals. The reaction was run under continuous stirring at 80 to 85° C. It took 8 hours for approximately 50% of the macromer to convert to the homopolymer and 16 hrs for approximately 70% of the macromer to convert to the homopolymer. $^1$H NMR analysis from CDCl$_3$ extract of the polymer product indicates that unreacted itaconic anhydride derivatives are in the product.

EXAMPLE II

Example I is repeated with the macromer of Example SM 7 (Table 1B) except that 0.5% of Luperox 11M 75 initiator (based on the total monomer weight) is added to the monomer mixture which is then heated to 60° C. In 10 minutes the reaction mass gels after reaching an exotherm of 72° C. The maleate derivative of DMC is much more reactive than the trisubstituted (methyl) maleate derivative of Example 1. $^1$H NMR analysis from CDCl$_3$ extract of this gel indicates that only a small portion of unreacted maleic anhydride remains in the reaction product.

The following examples illustrate the copolymerization of olefinically unsaturated dimethicone copolyol macromers (SM) of the invention with other olefinically unsaturated monomers such as AMPS, MMA, MAA and STY utilizing solution and precipitation polymerization techniques.

EXAMPLE III

A 500 ml jacketed reactor equipped with a condenser, thermocouple, mechanical stirring (half moon blade) and nitrogen blanket is charged with 2 parts of the dimethicone copolyol macromer of Example SM 9, 28.5 parts IPA, and 28.5 parts distilled water. Initiator (0.2 parts Luperox 11M75 in 1 part IPA) is injected into the reactor at 72° C. and a mixture of 18 parts AMPS 2405 monomer, 9 parts IPA, and 9 parts distilled water is metered in over 3 hours. An initiator booster (0.02 parts Luperox 11M75 in 1 part IPA) is added every hour after the metering commenced. Addition of booster continued until conversion of all reactants is confirmed by $^1$H NMR. A clear product is obtained by neutralizing with diluted AMP-95. The final product had 21.15% total solids content at pH 4.5.

EXAMPLE IV

A 500 ml jacketed reactor equipped as in Example III is charged with 15 parts of the dimethicone copolyol macromer of Example SM 9a, 380 parts distilled water and 100 parts of IPA. Initiator (0.4 parts Luperox 11M75 in 1 part IPA) is injected into the reactor at 80° C. and a mixture of 40 parts MMA and 20 parts MAA is metered into the reactor through a syringe pump. A mixture of 25 parts AMPS 2405 monomer and 25 parts water is metered into the reactor by another syringe pump over the course of 3 hours. An initiator booster (0.06 parts Luperox 11M75 in 1 part IPA) is added every hour after the metering commenced. The addition of booster continued until conversion of all reactants is confirmed by $^1$H NMR. The final product has a total solids content of 21.94% at pH 8.9 and appears as translucent liquid after stripping of the IPA and neutralizing with AMP-95.

EXAMPLE V

A 500 ml jacketed reactor equipped as in Example IV is charged with 5 parts of the dimethicone copolyol macromer of Example SM 9, 190 parts distilled water and 190 parts of IPA. Initiator (0.4 parts Luperox 11M75 in 1 part IPA) is injected into the reactor at 80° C. and a mixture of 55 parts styrene and 20 parts MAA is metered into the reactor through a syringe pump. A mixture of 20 parts AMPS 2405/10 parts water is injected into the reactor by another syringe pump over the course of 3 hours. An initiator booster (a total of 0.78 parts Luperox 11M75 in 1 part IPA) is added every hour after metering commenced. A polymer solid is obtained and is filtered and washed with 100 g IPA and followed by 50 g IPA/water mixture and then dried. The final product is a white powder.

The following examples illustrate copolymerization of the olefinically unsaturated dimethicone copolyol macromers (SM) of the invention with different types of monomers via anionic emulsion polymerization.

EXAMPLES VI to VIII

Emulsion polymers are prepared from the monomers set forth in Table 2 as follows: A monomer reaction mixture is prepared in a first reactor equipped with an agitator rotating at about 900 rpm under a nitrogen atmosphere by combining 148 parts by weight of MAA, about 200 parts by weight of EA, and about 40.0 parts by weight of the macromer prepared in Example SM 7 in 192 parts by weight of deionized water containing about 13.3 parts by weight of 30% aqueous sodium lauryl sulfate. To a second reactor equipped with a mixing agitator and nitrogen inlet and feed pumps, is added about 580 parts by weight of deionized water and about 1.27 parts by weight of 30% aqueous sodium lauryl sulfate. The contents of the second reactor are heated with agitation at a rotation speed of about 200 rpm under a nitrogen atmosphere. After the contents of the second reactor reach a temperature in the range of about 85 to 88° C., about 7.84 parts of a 1.73% ammonium persulfate solution (free radical initiator) is injected into the warmed surfactant solution in the second reactor. The aqueous emulsion of the monomer mixture from the first reactor is gradually pumped into the second reactor over a period of about 180 minutes at a temperature in the range of about 85 to 88° C. Simultaneously, an initiator feed about 60 parts by weight of 1.7% ammonium persulfate solution is metered to the reaction mixture in the second reactor and the temperature of the reaction is maintained at about 90° C. for an additional one and half hours to complete polymerization. The resulting emulsion is cooled to room temperature, discharged from the reactor and collected. All three copolymers are analyzed by $^1$H NMR using $CDCL_3$ extract.

TABLE 2

| Ex. No. | MAA (wt. %) | EA (wt. %) | SM (wt. %) | SM Type | $^1$H NMR ($CDCl_3$ extract) |
|---|---|---|---|---|---|
| VI | 37 | 53 | 10 | SM 7 | No free SM 7 |
| VII (comparative) | 37 | 53 | 10 | SM 6 | Free SM 6 |
| VIII | 37 | 53 | 10 | SM 9 | No free SM 9 |

The copolymer of comparative Example VII showed $^1$H NMR peaks corresponding to non-reactive succinate dimethicone copolyol ester which is presumably not incorporated into the copolymer. Surprisingly, the copolymers of Examples VI and VIII containing reactive double bonds did not show a functional ester peak related to unreacted maleate ester derivative (SM 7) or unreacted itaconate derivative of dimethicone copolyol ester (SM 9). These experiments illustrate that the macromers of the invention are readily copolymerizable in emulsion polymerization.

EXAMPLES 1 to 3

Emulsion polymers are prepared as in Examples VI to VIII utilizing the monomers and macromers set forth in Table 3. Three copolymers were synthesized using a non-reactive dimethicone copolyol (Silsoft® 475) in Example 3, the macromer SM 9 in Example 1, and no silicone additive in Example 2 to observe if incorporating the dimethicone copolyol macromers of the invention into a copolymer backbone has any affect on copolymer properties.

The viscosity of each polymer is measured at 1 and 2 percent solids mucilages neutralized with AMP-95 to pH 7. In addition Tg, clarity and turbidity (NTU) values are measured for each polymer. The results are reported in Table 3A.

TABLE 3

| Ex. No. | MMA level | Bam level | X-linker (level) | CSEM25[1] level | AAE5P5[2] level | MAA Level | EA level | SM Type (level) |
|---|---|---|---|---|---|---|---|---|
| 1 | 10 | 3 | TEGDMA (0.2) | 3 | 2 | 37 | 34.8 | SM 9 (10) |
| 2 (control) | 10 | 3 | TEGDMA (0.2) | 3 | 2 | 37 | 44.8 | No SM |
| 3 (comparative) | 10 | 3 | TEGDMA (0.2) | 3 | 2 | 37 | 34.8 | DMC[3] (10) |

[1]associative monomer
[2]semihydrophobic monomer
[3]Silsoft ® 475 dimethicone copolyol

TABLE 3A

| Ex. No. | Tg | 1% Viscosity (mPa·s) | Clarity (% T) | Turbidity (NTU) | 2% Viscosity (mPa·s), | Clarity (% T) | Turbidity (NTU) |
|---|---|---|---|---|---|---|---|
| 1a | 65 | 1,230 | 98 | 5 | 10,500 | | |
| 2a | 73 | 1,200 | 97 | 1 | 12,500 | 97.0 | 0.77 |
| 3a | 68 | 370 | 100 | 1 | 4,600 | | |

The viscosity efficiency of the polymer of Example 1 is maintained utilizing 10% weight percent of the dimethicone copolyol macromer of the invention. In contrast, the polymer of Example 3, which is made according to the teaching of U.S. Pat. No. 6,403,074 B1 containing 10 weight percent of a non-functionalized dimethicone copolyol has a lower viscosity at both 1 and 2 percent mucilages. The non-functionalized dimethicone copolyol (Silsoft® 475) might be acting as chain transfer agent in Example 3a and causing the viscosity deficiency of the resulting associative polymer.

EXAMPLES 4 to 6

Emulsion polymers are prepared as in Examples VI to VIII utilizing the monomers and macromers set forth in Table 4. The comonomers of Examples 4 and 5 are copolymerized in the presence of olefinically unsaturated dimethicone copolyol macromers of the invention, while the comonomers of comparative Example 6 are polymerized in the presence of a non-reactive (i.e., saturated dimethicone copolyol carboxylate). The polymers are compared for relative viscosity performance.

TABLE 4

| Ex. No. | MMA level | Bam level | X-linker (level) | CSEM25[1] level | AAE5P5[2] level | MAA level | EA level | SM Type (level) |
|---|---|---|---|---|---|---|---|---|
| 4 | 10 | 3 | TEGDMA (0.2) | 3 | 2 | 37 | 41.8 | SM 9 (3) |
| 5 | 10 | 3 | TEGDMA (0.2) | 3 | 2 | 37 | 41.8 | SM 7 (3) |
| 6 (comparative) | 10 | 3 | TEGDMA (0.2) | 3 | 2 | 37 | 41.8 | SM 6 (3) |

[1]hydrophobic monomer
[2]semihydrophobic monomer

The gel properties of each polymer are measured at 1 and 2 percent solids mucilages neutralized with AMP-95 to pH 7. When unsaturated functional dimethicone copolyol macromers (SM 9 and SM 7) are copolymerized into the associative polymer backbone, such polymers overcome the typical viscosity depression phenomenon exhibited by associative polymers containing saturated dimthicone copolyol (SM 6) as shown in Table 4A below. Glass transition and clarity values of the mucilages were maintained.

TABLE 4A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 4a | 70 | 700 | 96 | 4 | 8,350 | 94.8 | 1.64 |
| 5a | 69 | 1,000 | 96 | 1 | 7,750 | 94.0 | 0.24 |
| 6a | 69 | 370 | 99 | 1 | 3,800 | 98.0 | 0.53 |

EXAMPLES 7 to 10

Emulsion polymers are prepared as in Examples VI to VIII utilizing the monomers and macromers set forth in Table 5. In these examples the loading effect of the cyclic anhydride to the dimethicone copolyol in synthesizing the dimethicone copolyol macromer on the gel properties of the final copolymer product is determined and reported in Table 5A.

TABLE 5

| Ex. No. | MMA level | Bam level | X-linker (level) | CSEM25[1] level | AAE5P5[2] level | MAA level | EA level | SM Type (level) |
|---|---|---|---|---|---|---|---|---|
| 7 | 10 | 3 | TMPE015TA (0.25) | 3 | 0 | 40 | 43.8 | none |
| 8 | 10 | 3 | TMPE015TA (0.25) | 3 | 0 | 40 | 40.8 | SM 9 (3) |
| 9 | 10 | 3 | TMPE015TA (0.25) | 3 | 0 | 40 | 40.8 | SM 8 (3) |
| 10 | 10 | 3 | TMPE015TA (0.25) | 3 | 0 | 40 | 40.8 | SM 10 (3) |

[1]associative monomer
[2]semihydrophobic monomer

TABLE 5A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 7a | 78 | n/a | n/a | n/a | 9,650 | 97.0 | 0.89 |
| 8a | 77 | n/a | n/a | n/a | 9,750 | 98.0 | 0.43 |
| 9a | 75 | 1,100 | 96 | 0.89 | 1,260 | 98.0 | 0.39 |
| 10a | 74 | 12,280 | 96 | 1.3 | 10,300 | 96.0 | 0.38 |

The gel properties of each polymer are measured at 1 and 2 percent solids mucilages neutralized with AMP-95 to pH 7. From the data in Table 5A polymers polymerized from macromers synthesized from anhydride loading to dimethicone copolyol loadings of between 0.25 to 0.75 equivalents (based on the OH number of the dimethicone copolyol) give optimal gel properties.

EXAMPLES 11 and 12

Emulsion polymers are prepared as in Examples VI to VIII utilizing the monomers and macromers set forth in Table 6. Two copolymers were polymerized utilizing the monomers and macromers set forth in Table 6. The reactive dimethicone copolyol macromers of Examples SM 5 and SM 7 are synthesized from dimethicone copolyols of differing molecular weights (MW=2,500 and 19,000, respectively). Copolymers synthesized from low and high molecular weight dimethicone copolyol macromers give good sensory and gel properties.

TABLE 6

| Ex. No. | MMA level | Bam level | X-linker (level) | CSEM25[1] level | AAE5P5[2] level | MAA level | EA level | SM Type (level) |
|---|---|---|---|---|---|---|---|---|
| 11 | 10 | 3 | TMPEO15TA (0.25) | 3 | 0 | 40 | 40.8 | SM 7 (3) |
| 12 | 10 | 3 | TMPEO15TA (0.25) | 3 | 0 | 40 | 40.8 | SM 5 (3) |

[1]associative monomer
[2]semihydrophobic monomer

The gel properties of each polymer are measured at 1 and 2 percent solids mucilages neutralized with AMP-95 to pH 7. The data are presented in Table 6A.

TABLE 6A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 11a | n/a | 1,500 | 97.5 | 0.99 | 12,600 | 98 | 0.39 |
| 12a | n/a | 980 | 96 | 0.8 | 8,750 | 96 | 0.65 |

EXAMPLES 13 to 20

Emulsion polymers are prepared as in Examples VI to VIII utilizing the monomers and macromers set forth in Table 7. Several non-associative copolymers are synthesized utilizing dimethicone copolyol macromers containing terminal and pendant polyether groups that are fully functionalized with an unsaturated carboxylate group (R=R'=cyclic anhydride residue in Formula IIIa; z=y in Formula VIa) or partially functionalized with an unsaturated carboxylate group (one of R or R'=hydrogen in Formula IIIa; z≤y in Formula VIa). The viscosity of each polymer is measured at 1 and 2.5 percent solids mucilages neutralized with AMP-95 to pH 7. In addition Tg, clarity, and turbidity (NTU) values are measured for each polymer. The results are reported in Table 7A.

TABLE 7

| Ex. No. | Acrylate Monomer (level) | Amide Monomer (level) | X-linker (level) | MAA level | EA level | SM (level) |
|---|---|---|---|---|---|---|
| 13 | 0 | 0 | TMPTA (0.3) | 32 | 62.7 | SM 9 (5) |
| 14 | 0 | 0 | TMPTA (0.3) | 35 | 61.7 | SM 9 (3) |
| 15 | 0 | 0 | TMPTA (0.3) | 37 | 59.7 | SM 9 (3) |
| 16 | 0 | Bam (3) | TEGDMA (0.2) | 37 | 56.8 | SM 9 (3) |
| 17 | MMA (20) | Bam (3) | TEGDMA (0.2) | 37 | 36.8 | SM 9 (3) |
| 18 | MMA (15) | Oam (3) | TMPEO15TA (0.3) | 40 | 38.7 | SM 9 (3) |
| 19 | MMA (15) | Bam (3) | TMPEO15TA (0.3) | 40 | 38.7 | SM 9 (3) |
| 20 | TMCHMA (10) | Bam (3) | TMPEO15TA (0.2) | 40 | 43.8 | SM 9 (3) |
| 20a | 0 | 0 | TMPTA (0.3) | 35 | 59.7 | SM 3 (5) |
| 20b | 0 | 0 | TMPTA (0.3) | 35 | 59.7 | SM 4 (5) |
| 20c | 0 | 0 | TMPTA (0.3) | 35 | 59.7 | SM 1 (5) |
| 20d | 0 | 0 | TMPTA (0.3) | 35 | 59.7 | SM 2 (5) |

TABLE 7A

| Ex. No. | Tg | 1% Viscosity (mPa·s) | Clarity (% T) | Turbidity (NTU) | 2.5% Viscosity (mPa·s) | Clarity (% T) | Turbidity (NTU) |
|---|---|---|---|---|---|---|---|
| 13a | 45.6 | 2,660 | N/A | 29.4 | 7,650 | N/A | 9.3 |
| 14a | 54 | 720 | 93 | 5 | 2,400 | 91.0 | 3.10 |
| 15a | 59 | 640 | 95 | 4 | 1,500 | 95.0 | 2.20 |
| 16a | 81 | 105 | 100 | 0.7 | N/A | N/A | N/A |
| 17a | 87 | 57 | 100 | 0.71 | N/A | N/A | N/A |
| 18a | 85 | 280 | 94.0 | 2.27 | 360 | 95.0 | 2.07 |
| 19a | 88 | 220 | 98.0 | 0.59 | 280 | 97.0 | 0.54 |
| 20a | 83 | 200 | 96.0 | 1.53 | 980 | 94.0 | 1.88 |
| 20aa | 56.5 | 3,770 | 87.5 | 14.7 | 7,350 | 83.6 | 14 |
| 20ba | 58.8 | 7,550 | 81.1 | 36.9 | 16,200 | 70.1 | 31 |
| 20ca | N/A | 1,880 | 89.9 | 21.4 | 5,250 | 91.3 | 9.65 |
| 20da | N/A | 1,320 | 92.0 | 10.3 | 4,900 | 84.2 | 13.8 |

EXAMPLES 21 to 54

Emulsion polymers are prepared as in Examples VI to VIII utilizing the monomers and macromers set forth in Table 8. The viscosity of each polymer is measured at 2, 3, and 5 percent solids mucilages neutralized with AMP-95 to pH 7. In addition Tg, clarity and turbidity (NTU) values are measured for each polymer. The results are reported in Table 8A.

TABLE 8

| Ex. No. | Monomer (level) | Amide (level) | X-linker (level) | CSEM25[1] level | AAE5P5[2] level | MAA level | EA level | SM Type (level) |
|---|---|---|---|---|---|---|---|---|
| 21 | MMA (15) | Bam (3) | TEGDMA (0.2) | 3 | 0 | 40 | 35.8 | SM 9 (3) |
| 22 | MMA (10) | Bam (3) | TEGDMA (0.3) | 1 | 2 | 40 | 40.7 | SM 9 (3) |
| 23 | TMCHMA (10) | Bam (1) | TEGDMA (0.3) | 1 | 0 | 37 | 47.7 | SM 9 (3) |
| 24 | MMA (15) | Oam (3) | TMPEO15TA (0.3) | 1 | 2 | 37 | 38.7 | SM 9 (3) |

TABLE 8-continued

| Ex. No. | Monomer (level) | Amide (level) | X-linker (level) | CSEM25[1] level | AAE5P5[2] level | MAA level | EA level | SM Type (level) |
|---|---|---|---|---|---|---|---|---|
| 25 | MMA (10) | Oam (1) | TEGDMA (0.1) | 3 | 2 | 37 | 43.9 | SM 9 (3) |
| 26 | MMA (10) | Oam (3) | TMPEO15TA (0.2) | 1 | 0 | 37 | 45.8 | SM 9 (3) |
| 27 | TMCHMA (15) | Bam (3) | TMPEO15TA (0.3) | 1 | 0 | 40 | 37.7 | SM 9 (3) |
| 28 | TMCHMA (10) | Bam (3) | TEGDMA (0.1) | 3 | 0 | 37 | 43.9 | SM 9 (3) |
| 29 | MMA (15) | Oam (1) | TMPEO15TA (0.1) | 3 | 2 | 37 | 38.9 | SM 9 (3) |
| 30 | TMCHMA (10) | Oam (3) | TMPEO15TA (0.1) | 1 | 2 | 40 | 40.9 | SM 9 (3) |
| 31 | TMCHMA/MMA (5/5) | Bam (3) | TMPEO15TA (0.15) | 1 | 1.8 | 40 | 41.1 | SM 9 (3) |
| 32 | TMCHMA/MMA (5/5) | Oam (3) | TMPEO15TA (0.15) | 1 | 1.8 | 40 | 41.1 | SM 9 (3) |
| 33 | MMA (15) | Oam (3) | TMPEO15TA (0.2) | 1 | 0 | 37 | 40.8 | SM 9 (3) |
| 34 | MMA (10) | Bam (3) | TMPEO15TA (0.25) | 3 | 0 | 40 | 42.8 | SM 9 (1) |
| 35 |  |  | TMPEO15TA (0.3) | 1 | 0 | 40 | 56.9 | SM 9 (1.8) |
| 36 | MMA (10) | Bam (3) | TMPEO15TA (0.25) | 3 | 0 | 40 | 41.8 | SM 9 (2) |
| 37 | MMA (10) | Bam (3) | TMPEO15TA (0.25) | 3 | 0 | 40 | 40.8 | SM 9 (3) |
| 38 | MMA (10) | Bam (3) | TMPEO15TA (0.25) | 2 | 0 | 40 | 41.8 | SM 9 (3) |
| 39 | MMA (10) | Bam (3) | TMPEO15TA (0.3) | 1 | 0 | 40 | 42.7 | SM 9 (3) |
| 40 | MMA (10) | Bam (3) | TMPEO15TA (0.3) | 1.5 | 0 | 40 | 42.2 | SM 9 (3) |
| 41 |  |  | TMPEO15TA (0.3) | 1 | 0 | 40 | 55.7 | SM 9 (3) |
| 42 |  | Oam (1.8) | TMPEO15TA (0.3) | 1 | 0 | 40 | 53.9 | SM 9 (3) |
| 43 |  | Oam (4) | TMPEO15TA (0.3) | 1 | 0 | 40 | 51.7 | SM 9 (3) |
| 44 | WAM II (1.3) |  | TMPEO15TA (0.3) | 1 | 0 | 40 | 54.4 | SM 9 (3) |
| 45 | WAM II (2.9) |  | TMPEO15TA (0.3) | 1 | 0 | 40 | 52.8 | SM 9 (3) |
| 46 | MMA (52) |  |  | 0 | 0 | 35 | 10 | SM 9 (3) |
| 47 | MMA (10) | Bam (3) | TEGDMA (0.2) | 6 | 2 | 37 | 38.8 | SM 9 (3) |
| 48 |  |  | TMPEO15TA (0.3) | 1 | 0 | 40 | 53.7 | SM 9 (5) |
| 49 |  |  | TMPEO15TA (0.3) | 1 | 0 | 40 | 51.2 | SM 9 (7.5) |
| 50 |  |  | TMPEO15TA (0.3) | 1 | 0 | 40 | 48.7 | SM 9 (10) |
| 51 |  |  | TMPEO15TA (0.3) | 1 | 0 | 40 | 53.7 | SM 3 (5) |
| 52 |  |  | TMPEO15TA (0.3) | 1 | 0 | 40 | 53.7 | SM 4 (5) |
| 53 |  |  | TMPEO15TA (0.3) | 1 | 0 | 40 | 53.7 | SM 2 (5) |
| 54 |  |  | TMPEO15TA (0.3) | 1 | 0 | 40 | 53.7 | SM 1 (5) |

[1] associative monomer
[2] semihydrophobic monomer

TABLE 8A

| Ex. No. | Tg | 2% Viscosity (mPa·s) | Clarity (% T) | Turbidity (NTU) | 3% Viscosity (mPa·s) | Clarity (% T) | Turbidity (NTU) | 5% Viscosity (mPa·s) | Clarity (% T) | Turbidity (NTU) |
|---|---|---|---|---|---|---|---|---|---|---|
| 21a | 84 | 5,600 | 97.0 | 2.07 | 25,600 | 96.0 | 2.92 | 115,000 | 89.0 | 3.95 |
| 22a | 79 | 1,320 | 98.9 | 0.38 | 5,150 | 98.2 | 0.60 | 15,300 | 96.9 | 0.68 |
| 23a | 71 | 1,680 | 96.0 | 3.62 | 9,800 | 94.0 | 5.53 | 52,000 | 90.0 | 8.52 |

TABLE 8A-continued

| Ex. No. | Tg | 2% Viscosity (mPa·s) | Clarity (% T) | Turbidity (NTU) | 3% Viscosity (mPa·s) | Clarity (% T) | Turbidity (NTU) | 5% Viscosity (mPa·s) | Clarity (% T) | Turbidity (NTU) |
|---|---|---|---|---|---|---|---|---|---|---|
| 24a | 78 | 2,740 | 97.0 | 2.00 | 8,700 | 93.0 | 1.77 | 15,000 | 93.0 | 2.28 |
| 25a | 70 | 10,000 | 94.0 | 0.95 | 35,200 | 95.0 | 0.92 | 78,000 | 93.0 | 0.95 |
| 26a | 72 | 1,800 | 99.0 | 0.52 | 5,500 | 98.0 | 0.59 | 14,000 | 97.0 | 0.68 |
| 27a | 91 | 2,680 | 82.0 | 8.40 | 15,500 | 83.0 | 6.48 | 92,000 | 88.0 | 5.77 |
| 28a | 73 | 10,600 | 94.0 | 3.04 | 38,000 | 94.0 | 2.32 | 104,000 | 88.0 | 3.04 |
| 29a | 73 | 14,900 | 98.0 | 0.77 | 40,500 | 91.0 | 1.00 | 92,000 | 94.0 | 1.20 |
| 30a | 79 | 840 | 97.0 | 1.88 | 5,850 | 96.0 | 1.84 | 30,000 | 93.0 | 3.57 |
| 31a | 76 | 720 | 98 | 0.78 | 2,400 | 97 | 0.98 | 8,250 | 97 | 1.18 |
| 32a | 75 | 540 | 97.0 | 0.77 | 1,900 | 96 | 0.91 | 7,050 | 94 | 1.28 |
| 33a | 78 | 860 | 99.0 | 0.3 | 3,100 | 99.0 | 0.26 | 8,300 | 98.0 | 0.31 |
| 34a | 77 | 10,400 | 97.0 | 0.53 | 32,700 | 96.0 | 0.54 | 104,000 | 95.0 | 0.59 |
| 35a | 60 | 4,980 | 96.0 | 1.01 | 13,500 | 95 | 0.83 | 28,000 | 94 | 0.81 |
| 36a | 77 | 8,250 | 98.0 | 0.33 | 27,900 | 97.0 | 0.38 | 93,000 | 96.0 | 0.56 |
| 37a | 78 | 10,200 | 97.0 | 0.45 | 25,300 | 97.5 | 0.42 | 86,000 | 95 | 0.75 |
| 38a | 84 | 5,400 | 97.5 | 0.48 | 20,900 | 96.5 | 0.67 | 68,000 | 95.5 | 0.6 |
| 39a | 81 | 3,100 | 98.0 | 0.41 | 8,800 | 98 | 0.42 | 29,100 | 96 | 0.99 |
| 40a | 85 | 5,200 | 97.0 | 0.61 | 29,100 | 96 | 0.99 | 75,000 | 94 | 1.28 |
| 41a | 61 | 6,700 | 93.0 | 1.63 | 17,000 | 93 | 1.74 | 49,000 | 90 | 1.93 |
| 42a | 59 | 3,060 | 98.4 | 2.03 | 7,450 | 97.8 | 2.85 | 25,600 | 97.5 | 2.48 |
| 43a | 60 | 2,200 | 98.3 | 1.09 | 5,300 | 98.9 | 1.23 | 14,400 | 96 | 1.77 |
| 44a | 60 | 24,500 | 89.0 | 22.1 | 46,000 | 89.7 | 11.37 | 93,000 | 90 | 6.44 |
| 45a | 60 | 11,800 | 88.5 | 5.01 | 24,500 | 90.1 | 2.81 | 50,500 | 90 | 2.9 |
| 46a | 121 | 1200 | n/a | 83 | n/a | n/a | n/a | n/a | n/a | n/a |
| 47a | 45 | 35,200 | 95.7 | 1.75 | n/a | n/a | n/a | n/a | n/a | n/a |
| 48a | 64.5 | 3,020 | 98.7 | 0.1 | 3,020 | 98.7 | 0.11 | n/a | n/a | n/a |
| 49a | 65.9 | 2,110 | 98 | 0.5 | 2,110 | 98 | 0.54 | n/a | n/a | n/a |
| 50a | 33.3 | 2,110 | 96.1 | 1.3 | 2,110 | 96.1 | 1.28 | n/a | n/a | n/a |
| 51a | 64.5 | 1,220 | 95 | 6.9 | 1,220 | 95 | 6.86 | n/a | n/a | n/a |
| 52a | 66.0 | 1,530 | 95.6 | 6.3 | 1,530 | 95.6 | 6.3 | n/a | n/a | n/a |
| 53a | 68.6 | 5,000 | 97.8 | 3.02 | n/a | n/a | n/a | n/a | n/a | n/a |
| 54a | 68.3 | 9,550 | 99.5 | 3.0 | n/a | n/a | n/a | n/a | n/a | n/a |

EXAMPLES 55 to 59

Cationic acid-swellable associative emulsion polymers are polymerized from the monomers and macromers set forth in Table 9 according to the following procedure.

A monomer emulsion is prepared by adding (with mixing) the monomers in Table 9 into a reactor containing about 340 parts by weight of water, about 5.5 parts by weight of Emulsogen® EPN 407 nonionic surfactant and about 0.3 parts by weight of sodium lauryl sulfate (30%) anionic surfactant. The resulting mixture is agitated (about 400 rpm) at a temperature in the range of about 20 to about 25° C. under a nitrogen atmosphere until an emulsion is obtained. A solution of about 0.12 parts by weight of Bruggolite® FF6 (reducing agent) in about 5.0 parts by weight of water is then added to the monomer emulsion, with mixing agitation, to initiate the polymerization reaction. A solution of about 0.16 parts by weight of sodium persulfate (oxidizing agent) in about 5.0 parts by weight of water is then added to the monomer emulsion with mixing agitation to initiate the polymerization reaction. The temperature of the reaction mixture is maintained at a temperature in the range of about 60 to about 70° C. for about 2.5 hours after addition of the initiator. Additional quantities of initiator are added at about 0.5 hours and about 1.5 hours after the reaction is initiated (about 0.08 parts by weight of sodium persulfate in about 3.0 parts by weight of water for each additional quantity of initiator added).

The resulting polymer emulsion is cooled to a temperature in the range of about 44 to about 46° C. over a period of about 45 minutes and an oxidizing solution is added to the reaction mixture in two portions at one hour intervals thereafter. Each oxidizing (redox) solution contains about 0.15 parts by weight of t-butylhydroperoxide (70%), about 0.015 parts by weight of sodium lauryl sulfate (30%) and about 0.15 parts by weight of Bruggolite® FF6 reducing agent in about nine parts by weight of water. The polymer emulsions are cooled to ambient room temperature and discharged from the reactor.

TABLE 9

| Ex. No. | TEGDMA level | HEMA level | CSEM25[1] level | RAL 307 level | DMAEMA level | EA level | SM 9 level |
|---|---|---|---|---|---|---|---|
| 55 | 0.1 | 1.8 | 0 | 4 | 35 | 58.1 | 1 |
| 56 | 0.1 | 1.8 | 0 | 4 | 35 | 56.1 | 3 |
| 57 | 0.1 | 1.8 | 0 | 4 | 35 | 49.1 | 10 |
| 58 | 0.1 | 1.8 | 3 | 4 | 35 | 55.1 | 1 |
| 59 | 0.1 | 1.8 | 3 | 4 | 35 | 53.1 | 3 |

[1] associative monomer

The viscosity and clarity properties of each of the polymers are measured at 2 percent solids mucilages neutralized to pH 4 with a 50 percent solution of glycolic acid. The results are reported in Table 9A.

TABLE 9A

| Ex. No. | 2% Viscosity (mPa·s), | Yield Value (dynes/cm$^2$) | Turbidity (NTU) |
|---|---|---|---|
| 55a | 11,100 | 1,280 | 7.73 |
| 56a | 11,400 | 1,460 | 8.63 |
| 57a | 9,050 | 1,330 | 9.99 |
| 58a | 17,700 | 2,230 | 5.78 |
| 59a | 16,000 | 1,890 | 4.85 |

EXAMPLES 60 to 62

Precipitation polymerization reactions are conducted in a water jacketed two liter Pyrex® resin kettle equipped with mechanical stirrer, a thermometer and reflux condenser topped with a nitrogen inlet connected to a bubbler to provide a slightly positive pressure of nitrogen throughout the polymerization. The water jacket is connected to a constant temperature circulator. The resin kettle is charged with an azeotropic mixture of ethyl acetate, cyclohexane, along with the polymerizable monomers acrylic acid, silicone macromer (SM 9a) and allylpentaerythritol in the levels (parts by wt.) shown in Table 10. The mixture is sparged with nitrogen for 30 minutes while the reactor is heated to 45° C. At 45° C., the sparging tube is removed while a nitrogen purge is maintained. Under stirring di-(2-ethylhexyl)-peroxydicarbonate (in an amount of 0.275 to 0.98 grams) is added to the mixture. Polymerization is evident in a matter of minutes as the solution becomes hazy with precipitated polymer. After a few hours the mixture forms a thick slurry. The polymerization is continued for a total of 8 hours. The polymer slurry is transferred to a single neck flask and the solvent is removed by a rotary evaporator at 65° C. to 102° C. at 27 inches of vacuum. The obtained dry polymer product is a fine white powder. When dispersed in water, the polymer hydrates, and when neutralized with base becomes a thickened aqueous solution.

TABLE 10

| Ex. No. | AA level | SM9a level | APE level | Polymer Solids (wt. %) |
|---|---|---|---|---|
| 60 | 96.35 | 3 | 0.65 | 12 |
| 61 | 94.52 | 5 | 0.48 | 12 |
| 62 | 94.70 | 5 | 0.3 | 17 |

Mucilages of each polymer are prepared by neutralizing samples of 0.2, 0.5, and 1 wt. % (polymer solids) of each polymer in deionized water with an 18% aqueous solution of NaOH to a pH of about 7.5. The Brookfield viscosity and clarity value of each sample is measured and reported in Table 10a. Spindle sizes 5, 6, and 7 were employed for the viscosity measurements of the 0.2, 0.5, and 1 wt. % mucilages, respectively.

TABLE 10a

| Ex. No. | 0.2% mucilage Viscosity (mPa·s) | 0.5% mucilage Viscosity (mPa·s) | 1.0% mucilage Viscosity (mPa·s) | Clarity (0.5 wt % mucilage) |
|---|---|---|---|---|
| 60 | 16000 | 29500 | 52200 | 90.2 |
| 61 | 10600 | 26000 | 45200 | 90.0 |
| 62 | 10540 | 24200 | 36500 | 88.2 |

What is claimed is:

1. A polymer polymerized from a monomer composition comprising at least one dimethicone copolyol macromer selected from formulae III and IV below in combination with one or more monomers selected from:

a) at least one non-ionic vinyl monomer;

b) at least one acidic vinyl monomer;

c) at least one cationic vinyl monomer;

d) at least one associative vinyl monomer;

e) at least one semihydrophobic vinyl monomer;

f) at least one crosslinking monomer; and mixtures thereof

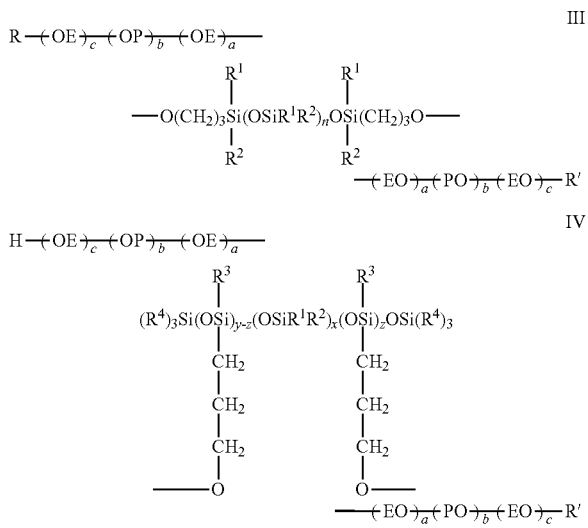

wherein in formula III R and R' independently represent hydrogen and a cyclic anhydride residue, subject to the proviso that R and R' do not both represent hydrogen at the same time, R$^1$ and R$^2$ independently represent a radical selected from C$_1$ to C$_{30}$ alkyl, C$_1$ to C$_{20}$ halo substituted alkyl, C$_3$ to C$_8$ cycloalkyl, C$_6$ to C$_{14}$ aryl, and C$_2$ to C$_{20}$ alkenyl, E represents a divalent ethylene radical, P independently represents a divalent propylene radical, a, b, and c are independently 0 to 100; and n is 0 to 200, E taken together with the oxygen atom to which is attached represents an ethylene oxide residue (EO or OE) and P taken together with the oxygen atom to which it is attached represents a propylene oxide residue (PO or OP) wherein the EO/PO and OE/OP residues can be arranged in random, non-random, or blocky sequences;

wherein in formula IV R$^1$ and R$^2$, E, P, a, b, and c are as defined above, R$^3$ represents a radical selected from C$_1$ to C$_{30}$ alkyl, C$_1$ to C$_{20}$ halo substituted alkyl, C$_3$ to C$_8$ cycloalkyl, C$_6$ to C$_{14}$ aryl, and C$_2$ to C$_{20}$ alkenyl, R$^4$ represents a radical selected from C$_1$ to C$_{30}$ alkyl, C$_6$ to C$_{14}$ aryl, and C$_2$ to C$_{20}$ alkenyl, x is 0 to 200, y is 1 to 200, z≤y; and wherein said cyclic anhydride residue in formulae III and IV is represented by the formula:

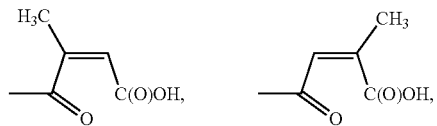

-continued

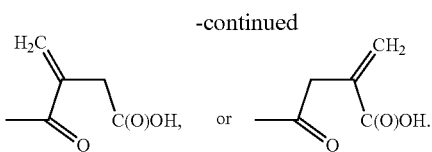

wherein R⁵ and R⁶ are independently selected from hydrogen and methyl, subject to the proviso that R⁵ and R⁶ do not both represent methyl at the same time.

2. A polymer of claim 1 wherein said non-ionic vinyl monomer is selected from at least one monomer represented by the formulae:

$$CH_2=C(X)Z;$$

$$CH_2=CH-OC(O)R^7$$

wherein, X is H or methyl; and Z is —C(O)OR⁸, —C(O)NH₂, —C(O)NHR⁸, —C(O)N(R⁸)₂, —C₆H₄R⁸, —C₆H₄OR⁸, —C₆H₄Cl, —C₆H₁₁, —C₆H₇(R⁸)(R⁸)(R⁸), —CN, —NHC(O)CH₃, —NHC(O)H, N-(2-pyrrolidonyl), N-caprolactamyl, —C(O)NHC(CH₃)₃, —C(O)NHCH₂CH₂—N-ethyleneurea, —Si(R⁷)₃, —C(O)O(CH₂)ₓSi(R⁷)₃, —C(O)NH(CH₂)ₓSi(R⁷)₃, or —(CH₂)ₓSi(R⁷)₃; x is an integer ranging from about 1 to about 6; R⁷ independently represents linear and branched C₁ to C₁₈ alkyl; R⁸ independently represents linear and branched C₁ to C₃₀ alkyl, hydroxy substituted C₂ to C₃₀ alkyl, and halogen substituted C₁ to C₃₀ alkyl.

3. A polymer of claim 1 wherein said acidic vinyl monomer contains at least one acidic group selected from the group consisting of a carboxylic acid group, a sulfonic acid group, a phosphonic acid group; and salts thereof.

4. A polymer of claim 3 wherein said acidic vinyl monomer is selected from the group consisting of acrylic acid, methacrylic acid, itaconic acid, citraconic acid, maleic acid, fumaric acid, crotonic acid, aconitic acid; C₁ to C₁₈ alkyl monoesters of maleic, fumaric acid, itaconic acid, aconitic acid; vinyl sulfonic acid, 2-sulfoethyl methacrylate, styrene sulfonic acid, 2-acrylamido-2-methylpropane sulfonic acid, allyloxybenzene sulfonic acid, vinyl phosphonic acid, allyl phosphonic acid, and 3-acrylamidopropyl phosphonic acid; and salts thereof; and mixtures thereof.

5. A polymer of claim 1 wherein said cationic vinyl monomer is selected from the group consisting of a mono-(C₁ to C₄)alkylamino(C₁ to C₈)alkyl (meth)acrylate, a di-(C₁ to C₄)alkylamino(C₁ to C₈)alkyl(meth)acrylate, a mono-(C₁ to C₄)alkylamino(C₁ to C₈)alkyl(meth)acrylamide, a di-(C₁ to C₄)alkylamino(C₁ to C₈)alkyl (meth)acrylamide, a nitrogen-containing heterocyclic (meth)acrylamide, and a nitrogen-containing heterocyclic (meth)acrylate; and salts thereof; and mixtures thereof.

6. A polymer of claim 5 wherein said cationic vinyl monomer is selected from the group consisting of 2-(N,N-dimethylamino)ethyl (meth)acrylate, 3-(N,N-dimethylamino) propyl (meth)acrylate, 4-(N,N-dimethylamino)butyl (meth)acrylate, (N,N-dimethylamino) -t-butyl(meth)acrylate, 2-tert-butylamino)ethyl(meth)acrylate, 2-(N,N-diethylamino) ethyl (meth)acrylate, 3-(N,N-diethylamino)propyl (meth)acrylate, 2-(N,N-dimethylamino) neopentyl acrylate, 4-N,N-diethylamino)butyl(meth)acrylate, 2-(N,N-dipropylamino) ethyl (meth)acrylate, 3-N,N-(dipropylamino)propyl (meth)acrylate, 4-N,N-dipropylamino)butyl (meth)acrylate, 3-(N,N-dimethylamino)propyl(meth)acrylate, 2-(4-morpholinyl) ethyl(meth)acrylate, 2-(4-morpholinyl)ethyl acrylate, N'-(2-N,N-dimethylamino)ethyl(meth)acrylamide, 2-(N,N-dimethylamino)propyl(meth)acrylamide, N'-3-(N, N-dimethylamino)propyl(meth)acrylamide, N-(2-pyridyl) acrylamide, N-2-imidazoyl)(meth)acrylamide, N-(4-morpholinyl)(meth)acrylamide, N-(4-morpholinyl)acrylamide, 2-vinyl pyridine, 4-vinyl pyridine, N-vinyl-2-methylimidazole, N-vinylimidazole, N-vinyl-4-methylimidazole, and N-vinyloxazolidone; and salts thereof; and mixtures thereof.

7. A polymer of claim 5 wherein said cationic vinyl monomer is selected from the group consisting of 3-trimethylammonium propyl(meth)acrylamide chloride, 3-trimethylammonium propyl acrylamide chloride, quaternized N,N-dimethylaminoethyl(meth)acrylate with C₁ to C₃₀ alkyl sulphate, quaternized N,N-dimethylaminoethyl(meth)acrylate with methylchloride, quaternized vinyl imidazole, methacryloyl ethyl betaine, and methacryloyl N-oxide.

8. A polymer of claim 1 wherein said associative vinyl monomer is selected from at least one monomer represented by the formula:

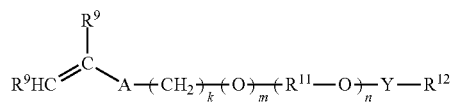

wherein, each R⁹ is independently H, C₁ to C₃₀ alkyl, —C(O)OH, or —C(O)OR¹⁰; R¹⁰ is C₁ to C₃₀ alkyl; A is —CH₂C(O)O—, —C(O)O—, —O—, —CH₂O—, —NHC(O)NH—, —C(O)NH—, —Ar—(CE₂)ᵤ—NHC(O)O—, —Ar—(CE₂)ᵤ—NHC(O)NH—, or —CH₂CH₂NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R¹¹—O)ₙ represents a polyoxyalkylene moiety of C₂ to C₄ oxyalkylene units, wherein R¹¹ is C₂H₄, C₃H₆, C₄H₈, or a mixture thereof, and n is an integer in the range of about 5 to about 250; Y is —R¹¹O—, —R¹¹NH—, —O(O)—, —C(O)NH—, —R¹¹NHC(O) NH—, or —C(O)NHC(O)—; and R¹² is a substituted or unsubstituted alkyl selected from a C₈ to C₄₀ linear alkyl, a C₈ to C₄₀ branched alkyl, a C₈ to C₄₀ carbocyclic alkyl, a C₂ to C₄₀ alkyl-substituted phenyl, an aryl-substituted C₂ to C₄₀ alkyl, and a C₈ to C₈₀ complex ester; wherein R¹¹ and R¹² optionally includes one or more substituents selected from hydroxyl, alkoxyl, and halogen.

9. A polymer of claim 8 wherein said associative vinyl monomer is selected from the group consisting of cetyl polyethoxylated methacrylate, cetearyl polyethoxylated (meth) acrylate, stearyl polyethoxylated (meth)acrylate, arachidyl polyethoxylated (meth)acrylate, behenyl polyethoxylated (meth)acrylate, lauryl polyethoxylated (meth)acrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenol polyethoxylated (meth)acrylate, hydrogenated castor oil polyethoxylated methacrylate, canola polyethoxylated (meth)acrylate, and cholesterol polyethoxylated (meth)acrylate, wherein the polyethoxylated portion of the monomer contains from about 5 to about 100 ethylene oxide repeating units.

10. A polymer of claim 1 wherein said semihydrophobic vinyl monomer is selected from at least one monomer represented by the formula:

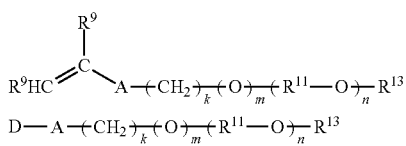

wherein $R^9$ is independently H, $C_1$ to $C_{30}$ alkyl, —C(O)OH, or —C(O)O$R^{10}$; $R^{10}$ is $C_1$ to $C_{30}$ alkyl; A is —$CH_2$C(O)O—, —C(O)O—, —O—, —$CH_2$O—, —NHC(O)NH—, —C(O)NH—, —Ar—$(CE_2)_z$—NHC(O)O—, —Ar—$(CE_2)_z$-NHC(O)NH—, or —$CH_2CH_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; ($R^{11}$—O)$_n$ represents a polyoxyalkylene moiety of $C_2$ to $C_4$ oxyalkylene units, wherein $R^{11}$ is $C_2H_4$, $C_3H_6$, $C_4H_8$, or a mixture thereof, and n is an integer in the range of about 5 to about 250; Y is —$R^{11}$O—, —$R^{11}$NH—, —C(O)—, —C(O)NH—, —$R^{11}$NHC(O)NH—, or —C(O)NHC(O)—; wherein $R^{11}$ optionally includes one or more substituents selected from hydroxyl, alkoxyl, and halogen; D is a $C_8$ to $C_{30}$ unsaturated alkyl, or a carboxy-substituted $C_8$ to $C_{30}$ unsaturated alkyl; and $R^{13}$ is H or $C_1$ to $C_4$ alkyl.

11. A polymer of claim 10 wherein said semihydrophobic vinyl monomer is represented by at least one monomer of the formulae:

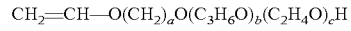

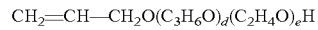

wherein a is an integer of 2, 3, or 4; b is an integer in the range of 1 to about 10; c is an integer in the range of about 5 to about 50; d is an integer in the range of 1 to about 10; and e is an integer in the range of about 5 to about 50.

12. A polymer of claim 1 wherein said monomer composition comprises 0 to 5 weight percent based on the weight of the total monomers of a crosslinking monomer.

13. A polymer of claim 1 wherein said monomer composition comprises at least 0.01 percent by weight based on the total monomer weight of a chain transfer agent.

\* \* \* \* \*